(12) United States Patent
Kawano

(10) Patent No.: US 10,779,712 B2
(45) Date of Patent: Sep. 22, 2020

(54) CAPSULE MEDICAL DEVICE GUIDANCE SYSTEM

(71) Applicant: OLYMPUS CORPORATION, Tokyo (JP)

(72) Inventor: Hironao Kawano, Machida (JP)

(73) Assignee: OLYMPUS CORPORATION, Tokyo (JP)

(*) Notice: Subject to any disclaimer, the term of this patent is extended or adjusted under 35 U.S.C. 154(b) by 601 days.

(21) Appl. No.: 15/630,796

(22) Filed: Jun. 22, 2017

(65) Prior Publication Data

US 2017/0280983 A1    Oct. 5, 2017

Related U.S. Application Data

(63) Continuation of application No. PCT/JP2016/056671, filed on Mar. 3, 2016.

(30) Foreign Application Priority Data

Apr. 17, 2015 (JP) .................. 2015-085384

(51) Int. Cl.
*A61B 5/00* (2006.01)
*A61B 1/04* (2006.01)
(Continued)

(52) U.S. Cl.
CPC .......... *A61B 1/041* (2013.01); *A61B 1/00057* (2013.01); *A61B 1/00158* (2013.01);
(Continued)

(58) Field of Classification Search
CPC ..... A61B 1/041; A61B 1/00057; A61B 1/045; A61B 1/00158; A61B 5/062; A61B 1/00039; A61B 1/00016
See application file for complete search history.

(56) References Cited

U.S. PATENT DOCUMENTS

2004/0236180 A1*  11/2004  Uchiyama .......... A61B 1/00158
                                                        600/109
2007/0219405 A1    9/2007  Uchiyama et al.
(Continued)

FOREIGN PATENT DOCUMENTS

CN           1747679 A     3/2006
JP        2004-255174 A    9/2004
(Continued)

OTHER PUBLICATIONS

International Search dated May 31, 2016 received in PCT/JP2016/056671.

*Primary Examiner* — Joel Lamprecht
(74) *Attorney, Agent, or Firm* — Scully Scott Murphy & Presser

(57) ABSTRACT

A capsule medical device guidance system includes: a capsule medical device including a permanent magnet and configured to be introduced into a subject; a magnetic field generator configured to generate a magnetic field to be applied to the capsule medical device; an operation input device configured to input operation information; and a processor including hardware. The processor is configured to: control the magnetic field generator, based on the operation information input from the operation input device, to change the magnetic field to change at least one of the position and the posture of the capsule medical device; obtain control information for the magnetic field generator in a state where forces acting on the capsule medical device are balanced before starting or when starting operation on the operation input device; and control the magnetic field generator by using the control information after the operation is finished.

15 Claims, 14 Drawing Sheets

(51) Int. Cl.
*A61B 1/00* (2006.01)
*A61B 1/045* (2006.01)
*A61B 5/06* (2006.01)

(52) U.S. Cl.
CPC .......... *A61B 1/045* (2013.01); *A61B 1/00016* (2013.01); *A61B 1/00039* (2013.01); *A61B 5/062* (2013.01)

(56) References Cited

U.S. PATENT DOCUMENTS

| | | |
|---|---|---|
| 2010/0010305 A1 | 1/2010 | Kawano |
| 2010/0030026 A1 | 2/2010 | Uchiyama et al. |
| 2011/0275893 A1 | 11/2011 | Kawano et al. |
| 2013/0006054 A1 | 1/2013 | Kawano |

FOREIGN PATENT DOCUMENTS

| | | |
|---|---|---|
| JP | 2006-68501 A | 3/2006 |
| JP | 2010-17555 A | 1/2010 |
| WO | 2011/055579 A1 | 5/2011 |

\* cited by examiner

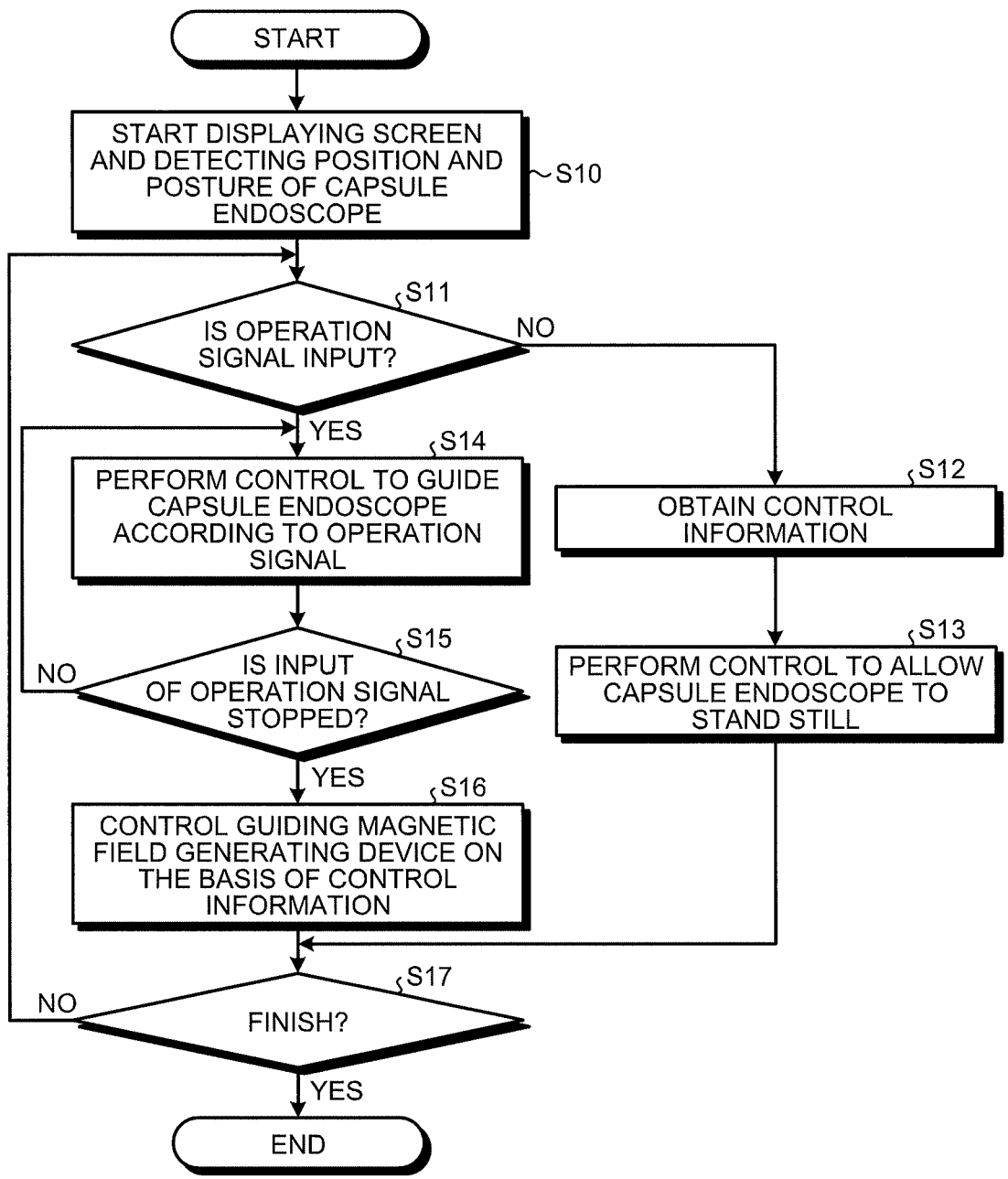

CAPSULE MEDICAL DEVICE GUIDANCE SYSTEM

CROSS-REFERENCE TO RELATED APPLICATIONS

This application is a continuation of PCT international application Ser. No. PCT/JP2016/056671 filed on Mar. 3, 2016 which designates the United States, incorporated herein by reference, and which claims the benefit of priority from Japanese Patent Application No. 2015-085384, filed on Apr. 17, 2015, incorporated herein by reference.

BACKGROUND

1. Technical Field

The disclosure relates to a capsule medical device guidance system which guides a capsule medical device introduced into a subject.

2. Related Art

Conventionally, a capsule medical device introduced into a subject having a function to obtain various pieces of information regarding the subject or give a medicine to the subject is developed. As an example, a capsule endoscope formed to have a size which may be introduced into a digestive tract of the subject is known in a field of the endoscope.

The capsule endoscope having an imaging function and a wireless communication function in a casing having a capsule shape is swallowed by the subject, then captures images while moving through the digestive tract by peristaltic motion and the like, and sequentially wirelessly transmits image data of images in an organ (hereinafter, also referred to as in-vivo images) of the subject. The wirelessly transmitted image data is received by a receiving device provided outside the subject to be captured by an image display device such as a work station and predetermined image processing is performed thereon. According to this, it is possible to display the in-vivo image of the subject as a still image or a moving image on a screen of the image display device.

Recently, a system of guiding the capsule medical device introduced into the subject by a magnetic field is suggested. For example, JP 2006-68501 A discloses a magnetic guidance medical system which introduces the capsule medical device in which a permanent magnet is incorporated into the subject and guides the capsule medical device by changing the magnetic field acting on the permanent magnet in the capsule medical device by moving a magnetic field generator provided outside the subject.

SUMMARY

In some embodiments, a capsule medical device guidance system includes: a capsule medical device including a permanent magnet provided inside the capsule medical device, the capsule medical device being configured to be introduced into a subject; a magnetic field generator provided outside the subject and configured to generate a magnetic field to be applied to the capsule medical device; an operation input device configured to input operation information for changing at least one of a position and a posture of the capsule medical device; and a processor including hardware. The processor is configured to: control the magnetic field generator, based on the operation information input from the operation input device, to change the magnetic field to change at least one of the position and the posture of the capsule medical device; obtain control information for the magnetic field generator in a state where forces acting on the capsule medical device are balanced before starting or when starting operation on the operation input device; and control the magnetic field generator by using the control information after the operation is finished.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 6 is a flowchart illustrating operation of the capsule medical device guidance system illustrated in FIG. 1;

DETAILED DESCRIPTION

Figure 1:
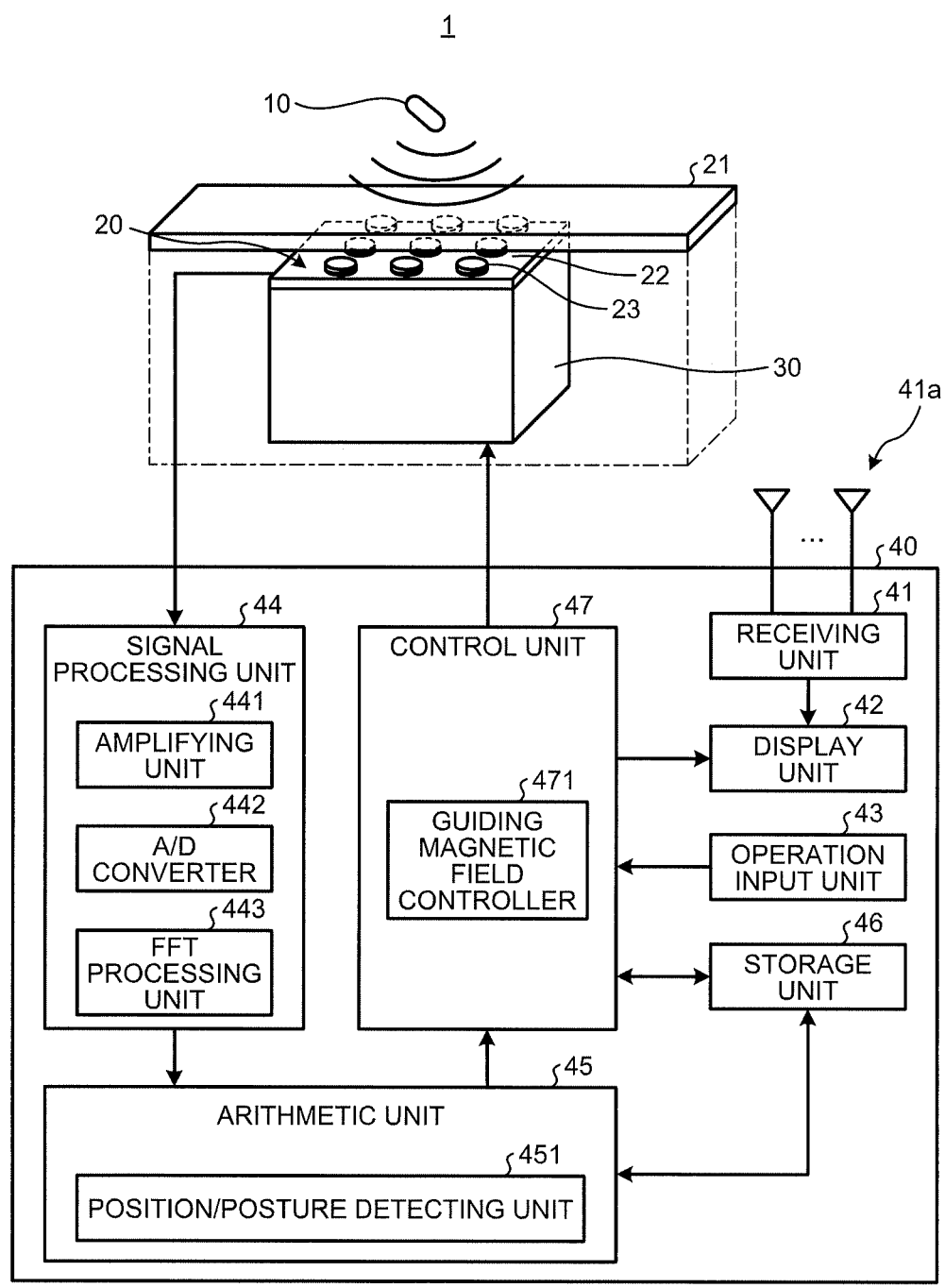
FIG. 1 is a view illustrating a configuration example of a capsule medical device guidance system according to a first embodiment of the disclosure.

A guidance device and a capsule medical device guidance system according to an embodiment of the disclosure are hereinafter described with reference to the drawings. Meanwhile, although a capsule endoscope which is orally introduced into a subject and captures an image in the subject (lumen) is illustrated as an embodiment of the capsule medical device to be guided by the capsule medical device guidance system according to this embodiment in the following description, the disclosure is not limited by the embodiment. That is to say, the disclosure is applicable to guidance of various medical devices having capsule shape such as a capsule endoscope which moves through the lumen from an esophagus to an anus of the subject, a capsule medical device which delivers a medicine and the like into the subject, and a capsule medical device provided with a pH sensor which measures pH in the subject, for example.

Also, in the following description, the drawings merely schematically illustrate shapes, sizes, and a positional relationship such that contents of the disclosure may be comprehended. Therefore, the disclosure is not limited only to the shapes, the sizes, and the positional relationship illustrated in the drawings. Meanwhile, in the drawings, the same part is assigned with the same reference sign.

First Embodiment

FIG. 1 is a schematic diagram illustrating an overview of a capsule medical device guidance system according to a first embodiment of the disclosure. As illustrated in FIG. 1, a capsule medical device guidance system 1 according to the first embodiment is provided with a capsule endoscope 10 as an example of the capsule medical device, a magnetic field detecting device 20 which detects a magnetic field for detecting a position of the capsule endoscope 10 arranged in the vicinity of a bed 21 on which the subject is placed, a guiding magnetic field generating device 30 as a magnetic field generator which generates a magnetic field for guiding the capsule endoscope 10 arranged in the vicinity of the bed 21, and a control device 40 which detects a position or a posture of the capsule endoscope 10 on the basis of a position detecting magnetic field detected by the magnetic field detecting device 20 and controls a guiding magnetic field of the capsule endoscope 10 on the basis of a detection result of the position or the posture.

Figure 2:
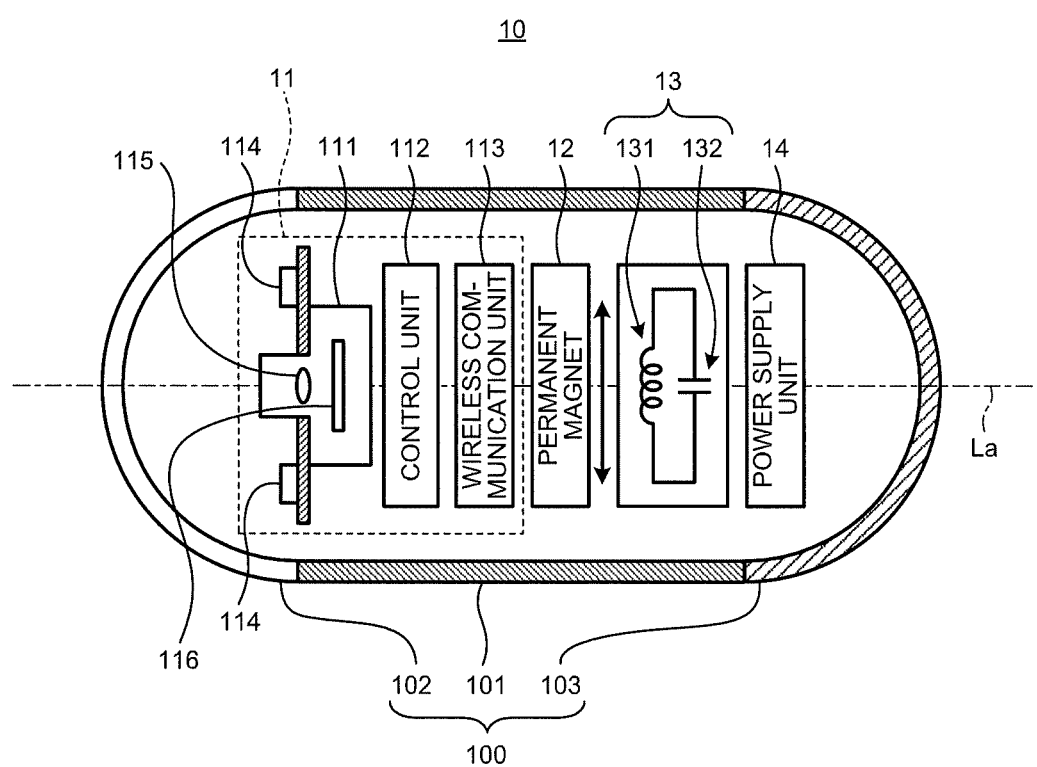
FIG. 2 is a schematic diagram illustrating an example of an inner structure of a capsule endoscope illustrated in FIG. 1.

FIG. 2 is a schematic diagram illustrating an example of an inner structure of the capsule endoscope 10 illustrated in FIG. 1. As illustrated in FIG. 2, the capsule endoscope 10 is provided with a casing 100 in a capsule shape formed to have a size easily introduced into the subject, and a function unit 11, a permanent magnet 12, a magnetic field generating unit 13 which generates the position detecting magnetic field of the capsule endoscope 10, and a power supply unit 14 which supplies electric power to each unit of the capsule endoscope 10 accommodated in the casing 100.

The casing 100 is an outer casing formed to have a size which may be introduced into an organ of the subject. The casing 100 including a cylindrical casing 101 having a cylindrical shape and dome-shaped casings 102 and 103 each having a dome shape is realized by closing open ends on both sides of the cylindrical casing 101 with the dome-shaped casings 102 and 103 each having the dome shape. In the first embodiment, the cylindrical casing 101 is formed of a colored member substantially opaque to visible light. Also, at least one of the dome-shaped casings 102 and 103 (in FIG. 2, the dome-shaped casing 102 on a side of an imaging unit 111 to be described later) is formed of an optical member transparent to light of a predetermined wavelength band such as the visible light. Such casing 100 hermetically includes the function unit 11, the permanent magnet 12, the magnetic field generating unit 13, and the power supply unit 14.

The function unit 11 is appropriately configured according to an application of the capsule medical device. When the capsule medical device is the capsule endoscope 10 which captures an image in the subject, the function unit 11 is provided with the imaging unit 111 which captures an image in the subject to obtain an imaging signal, a control unit 112 which controls operation of each unit of the capsule endoscope 10 including the imaging unit 111 and applies predetermined signal processing to the imaging signal obtained by the imaging unit 111, and a wireless communication unit 113 which wirelessly transmits the imaging signal to which the signal processing is applied.

The imaging unit 111 includes an illuminating unit 114 such as an LED, an optical system 115 such as a condenser lens, and an image sensor 116 such as a CMOS image sensor or a CCD image sensor. The illuminating unit 114 emits illumination light such as white light to an imaging field of view of the image sensor 116 to illuminate the subject in the imaging field of view across the dome-shaped casing 102. The optical system 115 condenses reflection light from the imaging field of view on an imaging surface of the image sensor 116 to form an image. The image sensor 116 converts the reflection light (optical signal) from the imaging field of view received on the imaging surface to an electric signal and outputs the same as an image signal.

Meanwhile, although one imaging unit 111 is provided only on a side of the dome-shaped casing 102 in FIG. 2, it is also possible to provide two imaging units 111; in this case, the dome-shaped casing 103 also is formed of the transparent optical member.

The control unit 112 allows the imaging unit 111 to operate at a predetermined imaging frame rate and allows the illuminating unit 114 to emit light in synchronization with the imaging frame rate. Also, the control unit 112 applies A/D conversion and other predetermined signal processing to the imaging signal generated by the imaging unit 111 to generate image data. Furthermore, the control unit 112 allows the power supply unit 14 to supply the electric power to the magnetic field generating unit 13, thereby allowing the magnetic field generating unit 13 to generate the position detecting magnetic field.

The wireless communication unit 113 provided with a transmitting antenna obtains the image data to which the signal processing is applied by the control unit 112 and relevant information and applies modulation processing thereto, then sequentially wirelessly transmits them to outside through the transmitting antenna.

Meanwhile, when the capsule medical device is a capsule for delivering a medicine into the subject, an accommodating unit which accommodates the medicine, a detecting unit which detects timing to deliver the medicine and the like are provided, for example, as the function unit 11. Alternatively, when the capsule medical device is a measuring capsule for measuring pH in the subject, a pH sensor, a wireless communication unit which wirelessly transmits a detection signal output from the pH sensor and the like are provided, for example, as the function unit 11.

The permanent magnet 12 which enables magnetic guidance of the capsule endoscope 10 by the guiding magnetic field generated by the guiding magnetic field generating device 30 is fixedly arranged in the casing 100 having the capsule shape such that a magnetization direction thereof is inclined with respect to a long axis La of the casing 100. Meanwhile, in FIG. 2, the magnetization direction of the permanent magnet 12 is indicated by an arrow. In the first embodiment, the permanent magnet 12 is arranged such that the magnetization direction thereof is orthogonal to the long axis La. The permanent magnet 12 operates so as to follow the magnetic field applied from outside, and as a result, the magnetic guidance of the capsule endoscope 10 by the guiding magnetic field generating device 30 is realized.

The magnetic field generating unit 13 including a magnetic field generating coil 131 through which current flows to generate a magnetic field forming a part of a resonance circuit and a capacitor 132 which forms the resonance circuit together with the magnetic field generating coil 131 is supplied with the electric power from the power supply unit 14 to generate an alternating magnetic field of a predetermined frequency as the position detecting magnetic field.

The power supply unit 14 being an electric storage unit such as a button battery and a capacitor includes a switch unit such as a magnetic switch and an optical switch. When the power supply unit 14 is configured to include the magnetic switch, this switches between an on-state and an off-state of the power supply by the magnetic field applied from outside and appropriately supplies the electric power in the electric storage unit to the function unit 11 and the magnetic field generating unit 13 in the on-state. Also, the power supply unit 14 stops supplying the electric power to the function unit 11 and the magnetic field generating unit 13 of the capsule endoscope 10 in the off-state.

With reference to FIG. 1 again, the magnetic field detecting device 20 is arranged below the bed 21. The magnetic field detecting device 20 detects the position detecting magnetic field generated by the magnetic field generating unit 13 of the capsule endoscope 10. The magnetic field detecting device 20 is provided with a panel 22 arranged so as to be parallel to an upper surface (surface on which the subject is placed) of the bed 21 and a plurality of detecting coils 23 arranged on the panel 22.

Each detecting coil 23 being a cylindrical coil obtained by winding a coil wire rod into a coil spring shape generates current according to the magnetic field distributed in its position and outputs the current as a detection signal of the magnetic field.

The guiding magnetic field generating device 30 generates the guiding magnetic field for changing at least one of the position and the posture of the capsule endoscope 10 introduced into the subject. Herein, the posture of the capsule endoscope 10 is represented by inclination (inclination angle) of the long axis La of the capsule endoscope 10 with respect to an axis (Z axis) in a gravity direction and a rotation angle (orientation angle) of the long axis La around the Z axis.

Figure 3:
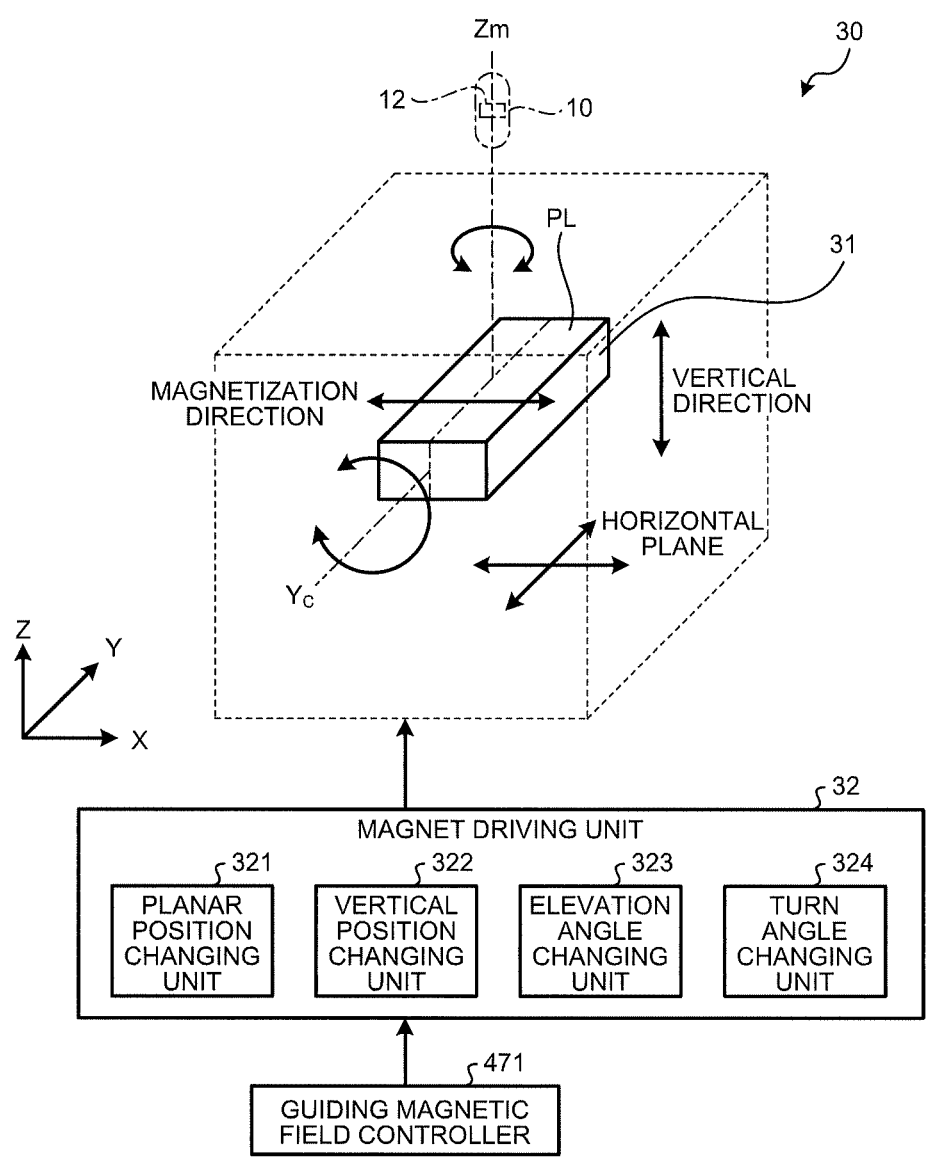
FIG. 3 is a schematic diagram illustrating a configuration example of a guiding magnetic field generating device illustrated in FIG. 1.

FIG. 3 is a schematic diagram illustrating a configuration of the guiding magnetic field generating device 30. As illustrated in FIG. 3, the guiding magnetic field generating device 30 is provided with a permanent magnet (hereinafter, referred to as an external permanent magnet) 31 which generates the magnetic field and a magnet driving unit 32 which changes a position and a posture of the external permanent magnet 31. Among them, the magnet driving unit 32 includes a planar position changing unit 321, a vertical position changing unit 322, an elevation angle changing unit 323, and a turn angle changing unit 324.

The external permanent magnet 31 is realized by a bar magnet having a cuboid shape, for example. The external permanent magnet 31 is arranged such that one surface (hereinafter, also referred to as a capsule opposing surface PL) among four surfaces parallel to the magnetization direction thereof is parallel to a horizontal plane (plane orthogonal to the gravity direction) in an initial state. Hereinafter, arrangement of the external permanent magnet 31 when the external permanent magnet 31 is in the initial state is referred to as reference arrangement.

The planar position changing unit 321 translates the external permanent magnets 31 in the horizontal plane (XY plane). That is to say, this moves in the horizontal plane in a state in which relative positions of two magnetic poles magnetized in the external permanent magnet 31 are ensured.

The vertical position changing unit 322 is a translating mechanism which translates the external permanent magnet 31 in the gravity direction (Z direction). That is to say, this moves in the vertical direction in the state in which the relative positions of the two magnetic poles magnetized in the external permanent magnet 31 are ensured.

The elevation angle changing unit 323 changes an angle of the magnetization direction with respect to the horizontal plane by rotating the external permanent magnet 31 in a vertical plane including the magnetization direction of the external permanent magnet 31. That is to say, the elevation angle changing unit 323 rotates the external permanent magnet 31 about an axis $Y_C$ in a Y direction passing through the center of the external permanent magnet 31 parallel to the capsule opposing surface PL and orthogonal to the magnetization direction.

The turn angle changing unit 324 rotates the external permanent magnet 31 about an axis Zm in the Z direction passing through the center of the external permanent magnet 31.

Figure 4:
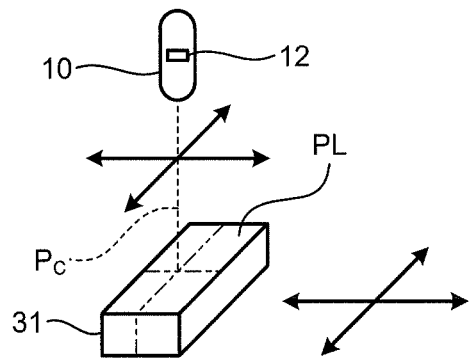
FIG. 4 is a schematic diagram for illustrating a method of guiding when the capsule endoscope is translated in a horizontal plane.
Figure 5A:
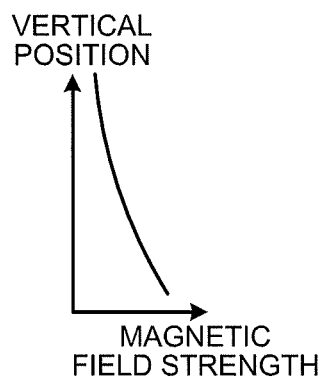
FIG. 5A is a view for illustrating a method of guiding when the capsule endoscope is translated in a vertical direction.
Figure 5B:
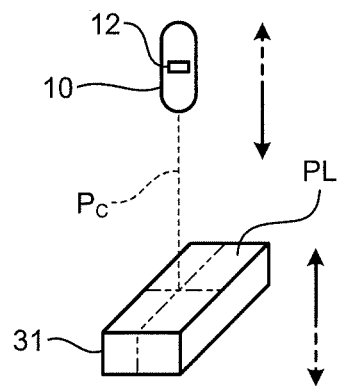
FIG. 5B is a view for illustrating a method of guiding when the capsule endoscope is translated in the vertical direction.

FIGS. 4, 5A, and 5B are schematic diagrams for illustrating a method of guiding the capsule endoscope 10. As illustrated in FIG. 4, when the capsule endoscope 10 is translated in a horizontal direction, a magnetic field which generates magnetic attracting force in a direction to trap the permanent magnet 12 in the capsule endoscope 10 in a specific position in the horizontal plane is generated and is allowed to act on the permanent magnet 12. It is possible to translate the capsule endoscope 10 in the horizontal direction by trapping the capsule endoscope 10 by attracting the permanent magnet 12 to the specific position and moving the external permanent magnet 31 in the horizontal plane by the planar position changing unit 321 in this state.

When the external permanent magnet 31 having the cuboid shape as illustrated in FIG. 4 is used, the capsule endoscope 10 is trapped on an axis $P_C$ passing through the center of the external permanent magnet 31 orthogonal to the capsule opposing surface PL. Also, when the magnetization direction of the permanent magnet 12 is orthogonal to the long axis La of the capsule endoscope 10 (refer to FIG. 2), the capsule endoscope 10 is trapped in a direction in which the long axis La is parallel to the axis $P_C$. Hereinafter, the axis $P_C$ on which the capsule endoscope 10 is trapped is referred to as a trapping axis $P_C$.

As illustrated in FIG. 5B, when the capsule endoscope 10 is translated in the vertical direction, as illustrated in FIG. 5A, the magnetic field magnetic gradient distribution of which changes according to a distance in a direction orthogonal to the capsule opposing surface PL is generated and is allowed to act on the permanent magnet 12 of the capsule endoscope 10. Specifically, when the external permanent magnet 31 is moved in the vertical direction by the vertical position changing unit 322 to change a distance between the external permanent magnet 31 and the permanent magnet 12, magnetic field strength acting from the external permanent magnet 31 to the permanent magnet 12 changes, so that the capsule endoscope 10 may be translated in the vertical direction.

When changing the inclination angle of the capsule endoscope 10, the elevation angle changing unit 323 rotates the external permanent magnet 31 about the axis $Y_C$ in a state in which the capsule endoscope 10 is trapped on the trapping axis $P_C$ (refer to FIG. 3). According to this, the trapping axis $P_C$ is inclined with respect to the vertical axis Zm and it is possible to incline the capsule endoscope 10 together with the trapping axis $P_C$.

Also, when turning the capsule endoscope 10, the turn angle changing unit 324 rotates the external permanent magnet 31 about the vertical axis Zm in the state in which the capsule endoscope 10 is trapped on the trapping axis $P_C$ (refer to FIG. 3). According to this, the trapping axis $P_C$ turns about the vertical axis Zm and it is possible to turn the capsule endoscope 10 together with the trapping axis $P_C$.

With reference to FIG. 1 again, the control device 40 formed of a general-purpose computer such as a personal computer and a work station, for example, detects the position and the posture of the capsule endoscope 10 on the basis of the detection signal output from the magnetic field detecting device 20 and controls the guiding magnetic field generating device 30 according to an operation input by a user on the basis of the detection result of the position and the posture, thereby guiding the capsule endoscope 10.

In detail, the control device 40 is provided with a receiving unit 41 which performs wireless communication with the capsule endoscope 10 to receive a wireless signal including the image signal transmitted from the capsule endoscope 10, a display unit 42 which applies predetermined signal processing to the image signal included in the wireless signal received by the receiving unit 41 to display the image signal in the subject, an operation input device 43 which accepts the input of the operation to the control device 40, a signal processing unit 44 which applies signal processing to the detection signal output from the magnetic field detecting device 20, an arithmetic unit 45 which performs arithmetic processing on the basis of the detection signal to which the signal processing is applied by the signal processing unit 44, a storage unit 46, and a control unit 47 which controls operation of each unit of the control device 40 and the capsule medical device guidance system 1.

The receiving unit 41 provided with a plurality of receiving antennas 41a sequentially receives the wireless signals from the capsule endoscope 10 through the receiving antennas 41a. The receiving unit 41 selects the antenna with the highest reception electric field strength among the receiving antennas 41a and performs modulation processing and the like on the wireless signal from the capsule endoscope 10 received through the selected antenna, thereby extracting the image signal from the wireless signal to output to the display unit 42.

The display unit 42 including a screen formed of various displays such as a liquid crystal display displays an image based on the image signal input from the receiving unit 41, positional information of the capsule endoscope 10, and other various pieces of information on the screen.

The operation input device 43 formed of an input device such as a joy stick, an operation table provided with various buttons and switches, and a keyboard inputs a signal according to externally performed operation to the control unit 47. Specifically, the operation input device 43 inputs the operation signal which changes at least any one of the position and the posture of the capsule endoscope 10 introduced into the subject to the control unit 47 according to the operation performed by the user.

The signal processing unit 44 includes a plurality of channels which processes the detection signals output from a plurality of detecting coils 23. Each channel is provided with an amplifying unit 441 which amplifies the detection signal output from the corresponding detecting coil 23, an A/D converter 442 which generates a digital detection signal by applying A/D conversion processing to the amplified detection signal, and a FFT processing unit 443 which applies fast Fourier transform (FFT) processing to the detection signal digital-converted by the A/D converter 442.

The arithmetic unit 45 is provided with a position/posture detecting unit 451 which performs arithmetic operation to detect the position and the posture of the capsule endoscope 10 from positions of a plurality of detecting coils 23 and strength and a phase of the magnetic field detected by each of the detecting coils 23 on the basis of a plurality of detection signals output from the signal processing unit 44. The position/posture detecting unit 451 outputs the detection result of the position and the posture of the capsule endoscope 10 to the control unit 47 as the positional information of the capsule endoscope 10 and stores the same in the storage unit 46.

Meanwhile, a method of detecting the position and the posture of the capsule endoscope 10 is not limited to the method of using the position detecting magnetic field. For example, it is also possible to detect the position and the posture of the capsule endoscope 10 on the basis of strength distribution of the wireless signals received by the receiving unit 41. As an example, it is possible to obtain the position of the capsule endoscope 10 by appropriately setting an initial value of the position of the capsule endoscope 10 and repeating processing to calculate an estimated value of the position by a Gaussian Newton's method until a shift amount between the calculated estimated value and a previously estimated value becomes a predetermined value or smaller (for example, refer to JP 2007-283001 A).

The storage unit 46 is formed of a storage medium which stores information so as to be rewritable such as a flash memory and a hard disk, a writing/reading device and the like. The storage unit 46 stores various programs and various parameters for controlling each unit of the control device 40 and an arithmetic program and the like for detecting the position and the posture of the capsule endoscope 10. Also, the storage unit 46 stores the positional information of the capsule endoscope 10 output from the arithmetic unit 45. Furthermore, it is also possible to store the image data of the image displayed on the display unit 42 in the storage unit 46.

The control unit 47 is provided with a guiding magnetic field controller 471 which controls operation of the guiding magnetic field generating device 30. The guiding magnetic field controller 471 outputs a control signal according to the operation signal input from the operation input device 43 to the guiding magnetic field generating device 30 on the basis of the positional information of the capsule endoscope 10 output from the arithmetic unit 45.

Operation of the capsule medical device guidance system 1 is next described. FIG. 6 is a flowchart illustrating operation of the control device 40. Also, FIGS. 7A to 7D are schematic diagrams for illustrating the method of guiding the capsule endoscope 10. FIG. 8 is a graph for illustrating a control method according to presence of an operation input to move the capsule endoscope 10 in the vertical direction. In the drawing, (a) of FIG. 8 illustrates the presence of the operation on the operation input device 43 (ON or OFF). Also, (b) of FIG. 8 illustrates magnetic attracting force Fm acting on the permanent magnet 12 in the capsule endoscope 10. The position in the vertical direction (Z direction) of the capsule endoscope 10 is illustrated in (c) of FIG. 8.

When the capsule endoscope 10 is powered on, the capsule endoscope 10 starts imaging operation and starts generating the position detecting magnetic field. According to this, at step S10, the control device 40 receives the wireless signal transmitted from the capsule endoscope 10 and starts displaying the image on the basis of the image signal included in the wireless signal. Also, the control device 40 detects the position detecting magnetic field transmitted from the capsule endoscope 10 and starts detecting the position and the posture of the capsule endoscope 10 on the basis of the detection signal. In this state, the user introduces the capsule endoscope 10 into the subject and performs operation to guide the capsule endoscope 10 by using the operation input device 43 while observing the image displayed on the display unit 42.

As illustrated in FIGS. 7A to 7D, the capsule endoscope 10 is introduced into the subject together with liquid W by oral intake and the like and executes predetermined operation such as imaging in a state of floating in the liquid W in an organ (stomach and the like) of the subject. The liquid W is liquid harmless to a human body such as water and normal saline, for example.

In the first embodiment, the capsule endoscope 10 is designed to have a specific gravity smaller than that of the liquid W and float on the liquid W in a state in which the magnetic field generated by the guiding magnetic field generating device 30 does not act. In the liquid W, it is possible to stop the capsule endoscope 10 in a position desired by the user or move the same to observe in the organ by balance of buoyancy Fb acting on the capsule endoscope 10, gravity Fg, and the magnetic attracting force Fm acting on the permanent magnet 12 by the guiding magnetic field.

At step S11, the control unit 47 determines whether the operation signal is input from the operation input device 43, that is to say, whether the operation input to guide the capsule endoscope 10 is performed.

When the operation signal is not input (step S11: No), the control unit 47 obtains control information indicating a current control state for the guiding magnetic field generating device 30 (step S12). Specifically, timing after the capsule endoscope 10 is introduced into the subject until initial operation is performed on the operation input device 43 (t=0 to $t_{11}$) or timing after the operation on the operation input device 43 is stopped (t is on or after $t_{13}$) corresponds to this case.

In the first embodiment, a position $Z=Z_1$ of the capsule endoscope 10 is obtained from the positional information output from the arithmetic unit 45 and the position of the external permanent magnet 31 provided on the guiding magnetic field generating device 30 is obtained, and magnetic attracting force $Fm=Fm_1$ determined by a distance between the capsule endoscope 10 and the external permanent magnet 31 is obtained as the control information. Alternatively, the distance between the capsule endoscope 10 and the external permanent magnet 31 may also be obtained as the control information.

At subsequent step S13, the guiding magnetic field controller 471 performs control to allow the capsule endoscope 10 to stand still on the guiding magnetic field generating device 30.

Figure 7A:
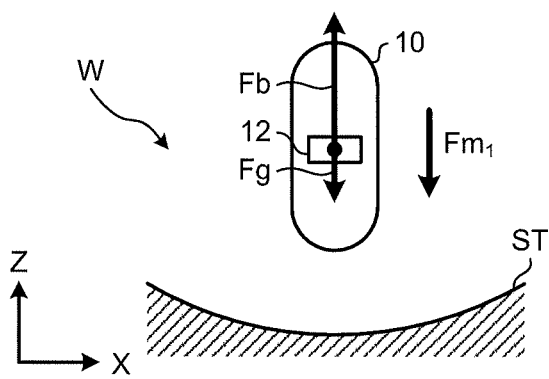
FIG. 7A is a schematic diagram for illustrating a method of guiding the capsule endoscope in the capsule medical device guidance system illustrated in FIG. 1.
Figure 8:
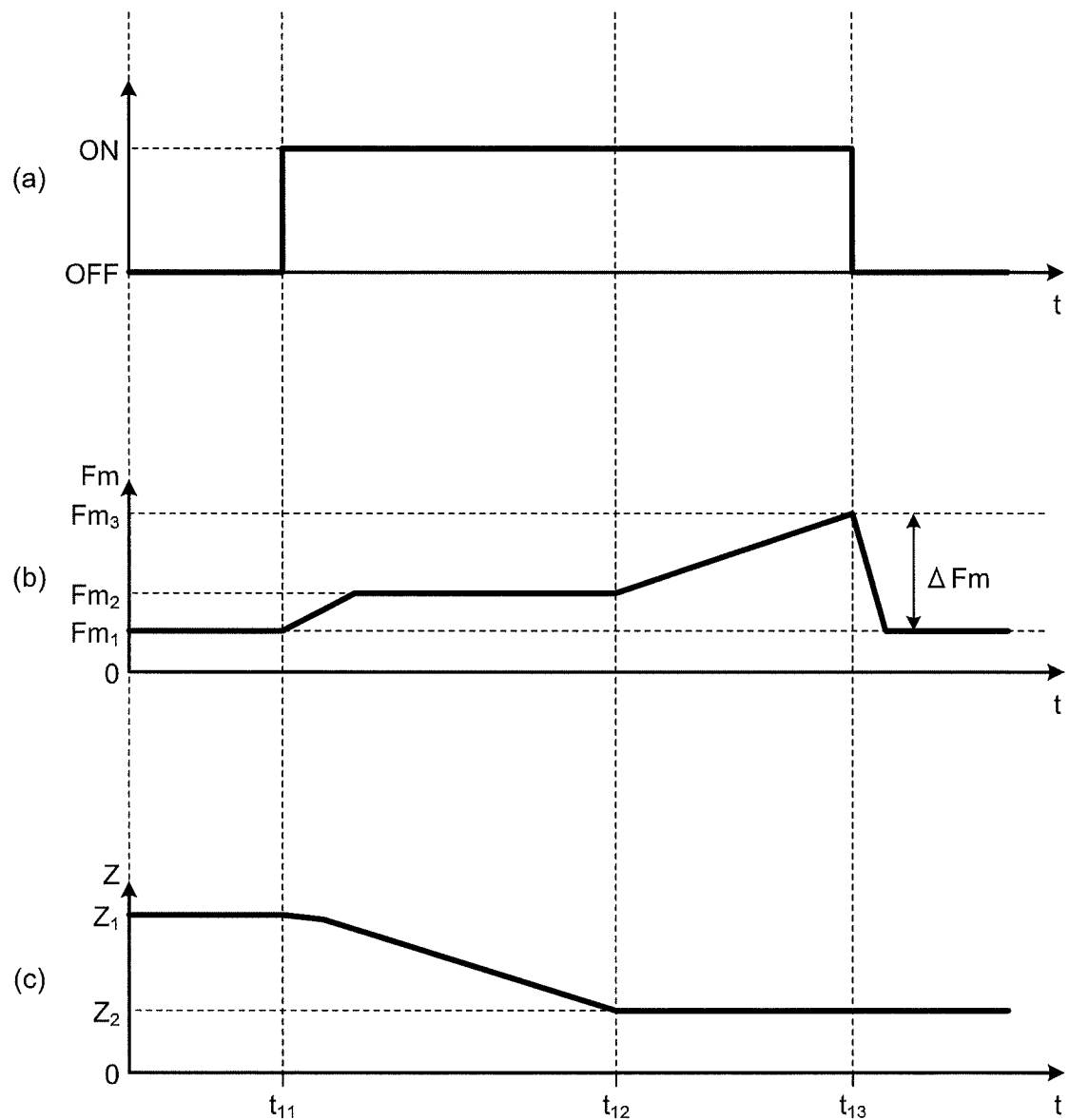
FIG. 8 is a graph for illustrating a control method according to presence of an operation input to move the capsule endoscope in the vertical direction.

As illustrated in FIG. 7A, the capsule endoscope 10 receives the buoyancy Fb, the gravity Fg, and the magnetic attracting force Fm by the guiding magnetic field in the liquid W introduced into the subject. When the three forces are balanced, the capsule endoscope 10 stably stands still in the liquid W. The guiding magnetic field controller 471 controls the guiding magnetic field generating device 30 on the basis of the positional information output from the arithmetic unit 45 to adjust the magnetic attracting force Fm acting on the capsule endoscope 10 such that change per unit time in position and posture of the capsule endoscope 10 becomes small, thereby allowing the capsule endoscope 10 to stand still. Thereafter, the operation of the control device 40 shifts to step S17 to be described later.

The control information is updated by repetition of steps S12 and S13 while the operation to guide the capsule endoscope 10 is not performed and the control information in a stable standing-still state in which the buoyancy Fb acting on the capsule endoscope 10, the gravity Fg, and the magnetic attracting force Fm are balanced is obtained. Such control information is obtained until the operation on the operation input device 43 is started.

On the other hand, when the operation signal is input from the operation input device 43 to the control unit 47 at step S11 (step S11: Yes), the guiding magnetic field controller 471 performs control to guide the capsule endoscope 10 according to the operation signal input from the operation input device 43 (step S14). Specifically, the guiding magnetic field generating device 30 is controlled such that the capsule endoscope 10 moves by an amount according to the operation in a direction according to the operation on the operation input device 43 to change the magnetic attracting force Fm acting on the capsule endoscope 10.

Figure 7B:
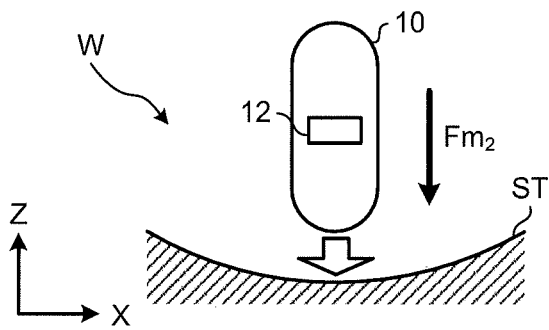
FIG. 7B is a schematic diagram for illustrating the method of guiding the capsule endoscope in the capsule medical device guidance system illustrated in FIG. 1.

For example, when the operation to guide the capsule endoscope 10 toward a bottom of the organ is input ($t=t_{11}$), the guiding magnetic field controller 471 controls the guiding magnetic field generating device 30 such that the magnetic attracting force Fm acting on the capsule endoscope 10 becomes stronger (Fm=$Fm_1 \rightarrow Fm_2$) as illustrated in FIG. 7B. That is to say, the external permanent magnet 31 is allowed to approach the subject.

At subsequent step S15, the control unit 47 determines whether the input of the operation signal from the operation input device 43 is stopped. When the operation signal is continuously input (step S15: No), the operation of the control unit 47 returns to step S14.

On the other hand, when the input of the operation signal is stopped (step S15: Yes), the guiding magnetic field controller 471 controls the guiding magnetic field generating device 30 on the basis of the control information obtained at step S12 (step S16).

Figure 7C:
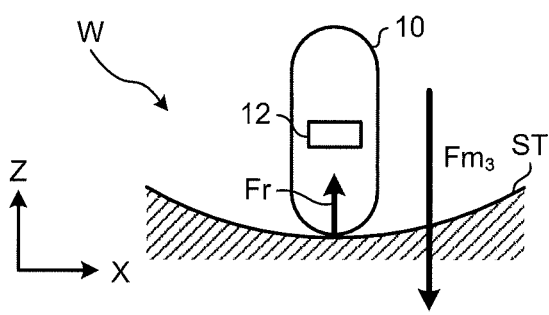
FIG. 7C is a schematic diagram for illustrating the method of guiding the capsule endoscope in the capsule medical device guidance system illustrated in FIG. 1.

Herein, a case in which the capsule endoscope 10 is brought into contact with an inner wall ST on the bottom of the liquid W as illustrated in FIG. 7C is considered. In this case, as illustrated in t=$t_{12}$ and thereafter in (c) of FIG. 8, the position of the capsule endoscope 10 remains unchanged from Z=$Z_2$. On the other hand, the user may merely indirectly recognize the position and the state of the capsule endoscope 10 in the subject by means of the positional information and the image in the subject displayed on the display unit 42. Therefore, the user continuously performs the operation on the operation input device 43 until the user recognizes that the capsule endoscope 10 is brought into contact with the inner wall ST. As a result, the magnetic attracting force Fm acting on the capsule endoscope 10 becomes larger.

At that time, the capsule endoscope 10 stands still by balance of the buoyancy Fb, the gravity Fg, the magnetic attracting force $Fm_3$, and vertical drag Fr received from the inner wall ST. In other words, the magnetic attracting force ΔFm and the vertical drag Fr are excessively applied in the state in which the buoyancy Fb, the gravity Fg, and the magnetic attracting force $Fm_1$ are balanced and the capsule endoscope 10 is stably stands still in the liquid W. That is to say, there is a gap between the state of the capsule endoscope 10 intended by the control for the guiding magnetic field generating device 30 (state in which this moves by the magnetic attracting force ΔFm if there is not the inner wall ST) and an actual state of the capsule endoscope 10 (state in which motion is blocked by the inner wall ST).

Thereafter, when the control state for the guiding magnetic field generating device 30 is left unchanged at a time the user stops the operation on the operation input device 43 (t=$t_{13}$), the gap between the state intended by the control for the guiding magnetic field generating device 30 and the actual state is maintained as it is. In this case, when operation to float the capsule endoscope 10 is performed next time, it is required to decrease the magnetic attracting force Fm acting on the capsule endoscope 10 to put the capsule endoscope 10 into the stable standing-still state (ΔFm=Fr=0) and thereafter start controlling the guiding magnetic field according to the operation on the operation input device 43. Therefore, responsiveness of the capsule endoscope 10 to the operation on the operation input device 43 is deteriorated.

Figure 7D:
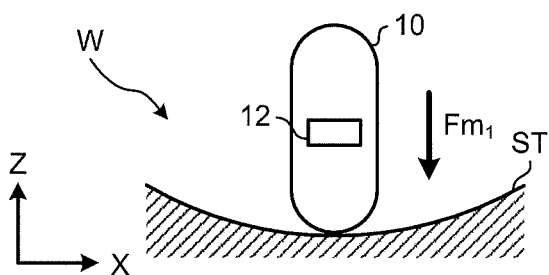
FIG. 7D is a schematic diagram for illustrating the method of guiding the capsule endoscope in the capsule medical device guidance system illustrated in FIG. 1.

Therefore, when the operation on the operation input device 43 is stopped (t=$t_{13}$), the guiding magnetic field controller 471 controls the guiding magnetic field generating device 30 on the basis of the control information obtained at step S12. In further detail, the guiding magnetic field controller 471 takes, as a basis, a state of the capsule endoscope 10 when the operation on the operation input device 43 is stopped, and performs control for reproducing the control state indicated by the control information on the basis of the state of the capsule endoscope 10 when the operation on the operation input device 43 is stopped. Specifically, as illustrated in FIG. 7D, the guiding magnetic field generating device 30 is allowed to adjust the position of the external permanent magnet 31 such that the magnetic attracting force acting on the capsule endoscope 10 becomes Fm=$Fm_1$ while the position of the capsule endoscope 10 is maintained as it is. According to this, the capsule endoscope 10 is put into the stable standing-still state and an input of next operation is waited.

At subsequent step S17, the control unit 47 determines whether to finish observing by the capsule endoscope 10. For example, when an instruction signal to finish observing by the capsule endoscope 10 is input from the operation input device 43, when the transmission of the wireless signal from the capsule endoscope 10 is stopped, or when the detection of the position detecting magnetic field from the capsule endoscope 10 is stopped, the control unit 47 determines to finish observing by the capsule endoscope 10 (step S17: Yes). In this case, the operation of the control device 40 finishes. On the other hand, when the observation by the capsule endoscope 10 is not finished (step S17: No), the operation of the control device 40 returns to step S11.

As described above, in the first embodiment of the disclosure, the control information indicating the control state before starting or when starting the operation on the operation input device 43 is obtained, and when the operation on the operation input device 43 is stopped, the guiding magnetic field generating device 30 is controlled on the basis of the control information. According to this, it is possible to eliminate the gap of the control generated during the operation and limit the state in which the buoyancy Fb acting on the capsule endoscope 10, the gravity Fg, and the magnetic attracting force $Fm_1$ are balanced and the capsule endoscope 10 stably stands still in the liquid W. Therefore, when the operation on the operation input device 43 is performed next time, the control may be started from the standing-still state, so that it becomes possible to improve the responsiveness of the capsule endoscope 10 to the operation.

Variation 1-1

A variation 1-1 of the first embodiment of the disclosure is described. In the above-described first embodiment, when operation on an operation input device 43 is finished (step S15: Yes), control based on a control state before starting or when starting the operation may be performed only when a gap between the control state at that time and the control state before starting or when starting the operation is large.

Specifically, when an input of an operation signal is stopped at step S15 (step S15: Yes), a control unit 47 calculates magnetic attracting force $Fm_3$ acting on a capsule endoscope 10 as the control information when the operation is finished from a positional relationship between the capsule endoscope 10 and an external permanent magnet 31 at that time. Then, a difference ΔFm between the magnetic attracting force $Fm_3$ and magnetic attracting force $Fm_1$ obtained as the control information at step S12 is calculated, and only when the difference ΔFm is larger than a threshold set in advance, the control based on the control information obtained at step S12 is performed.

Alternatively, when a distance between the capsule endoscope 10 and the external permanent magnet 31 is obtained as the control information at step S12, a difference between this distance and a distance between the capsule endoscope 10 and the external permanent magnet 31 when the operation finishes is calculated, and the control based on the control information obtained at step S12 is performed only when the difference is larger than a threshold.

Variation 1-2

A variation 1-2 of the first embodiment of the disclosure is described. Although a control unit 47 obtains control information indicating a current control state for a guiding magnetic field generating device 30 (step S12) when an operation signal is not input at step S11 (step S11: No) in the above-described first embodiment, it is also possible to obtain the control information after checking that a capsule endoscope 10 is in a stable standing-still state. In detail, the control unit 47 determines whether change per unit time in position and posture of the capsule endoscope 10 is not larger than a threshold on the basis of positional information of the capsule endoscope 10 output from an arithmetic unit 45, and when the change is not larger than the threshold, this determines that the capsule endoscope 10 is in the stable standing-still state and obtains the control information.

Variation 1-3

A variation 1-3 of the first embodiment of the disclosure is described. In the above-described first embodiment, it is also possible to use information obtained in advance by calibration in place of control information when an operation signal is not input (step S12) as the control information when a capsule endoscope 10 is in a stable standing-still state.

Figure 9:
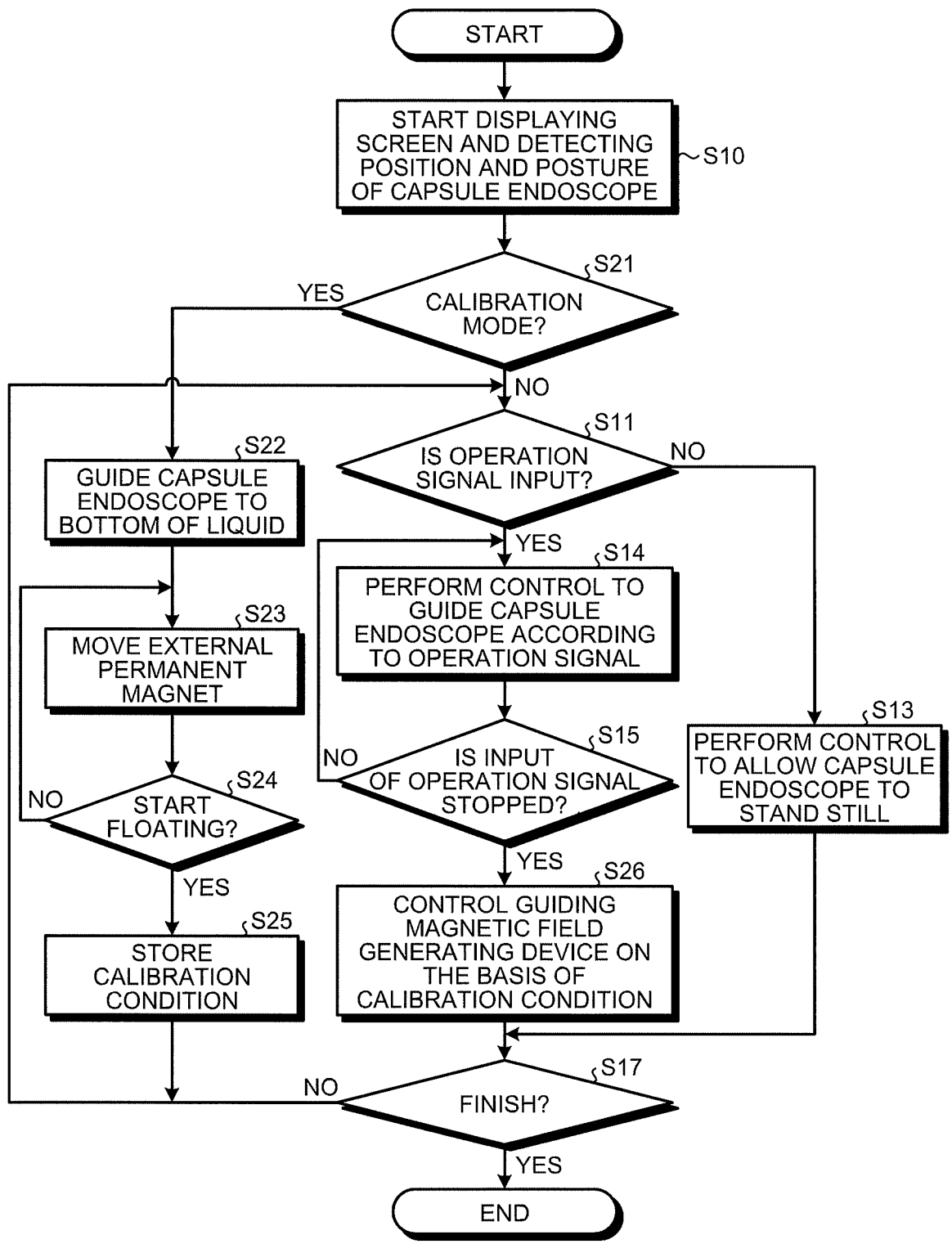
FIG. 9 is a flowchart illustrating operation of a control device in a variation 1-3 of the first embodiment of the disclosure.

FIG. 9 is a flowchart illustrating operation of a control device 40 in the variation 1-3. Meanwhile, step S10 illustrated in FIG. 9 is similar to that of the first embodiment (refer to FIG. 6).

At step S21 after step S10, a control unit 47 determines whether an instruction signal to switch to a calibration mode is input from an operation input device 43. When the instruction signal to switch to the calibration mode is input (step S21: Yes), a guiding magnetic field controller 471 performs control to guide the capsule endoscope 10 to a bottom of liquid W on a guiding magnetic field generating device 30 (step S22). The capsule endoscope 10 at that time may also be in a state of being pressed against an inner wall ST (state in which vertical drag Fr is generated) as illustrated in FIG. 7C.

At subsequent step S23, the guiding magnetic field controller 471 performs control to move an external permanent magnet 31 downward on the guiding magnetic field generating device 30 (step S23). According to this, magnetic attracting force Fm acting on the capsule endoscope 10 is made smaller. In the calibration mode, it is not required to allow the capsule endoscope 10 to stand still in water, so that a moving speed of the external permanent magnet 31 at that time may be fast to a certain degree.

At subsequent step S24, the control unit 47 determines whether the capsule endoscope 10 is separated from the inner wall ST and starts floating on the basis of positional information of the capsule endoscope 10 output from an arithmetic unit 45. This may be determined on the basis of change in Z axis of the capsule endoscope 10. Alternatively, it is also possible to determine by performing image processing such as pattern matching on an image in a subject displayed on a display unit 42 to detect change in the image.

When the capsule endoscope 10 does not yet start floating (step S24: No), the guiding magnetic field controller 471 continuously performs control to move the external permanent magnet 31 downward (step S23).

On the other hand, when the capsule endoscope 10 starts floating (step S24: Yes), the guiding magnetic field controller 471 obtains a position of the external permanent magnet 31 when the capsule endoscope 10 starts floating and stores a distance between the capsule endoscope 10 and the external permanent magnet 31 in a storage unit 46 as a calibration condition (step S25). Thereafter, the operation of the control device 40 shifts to step S11. Meanwhile, also when the instruction signal to switch to the calibration mode is not input (step S21: No), the operation of the control device 40 similarly shifts to step S11. Operation at step S11 is similar to that of the first embodiment.

When the operation signal is not input at step S11 (step S11: No), the operation of the control device 40 directly shifts to step S13. Operation at step S13 is similar to that of the first embodiment.

On the other hand, when the operation signal is input at step S11 (step S11: Yes), the operation of the control device 40 shifts to steps S14 and S15. Operation at steps S14 and S15 is similar to that of the first embodiment.

When the input of the operation signal is stopped at step S15 (step S15: Yes), the guiding magnetic field controller 471 obtains the calibration condition from the storage unit 46 and controls the guiding magnetic field generating device 30 on the basis of the calibration condition (step S26). That is to say, this allows the guiding magnetic field generating device 30 to adjust the position of the external permanent magnet 31 such that the distance between the capsule endoscope 10 and the external permanent magnet 31 becomes the distance therebetween when the capsule endoscope 10 starts floating from the bottom of the liquid W being the calibration condition. Step S17 thereafter is similar to that of the first embodiment.

According to the variation 1-3, the control on the guiding magnetic field generating device 30 is performed by using the calibration condition, so that a control state when the vertical drag Fr which the capsule endoscope 10 receives from the inner wall ST becomes zero, that is to say, the control state when magnetic attracting force Fm acting on the capsule endoscope 10, buoyancy Fb, and gravity Fg are balanced may be correctly reproduced.

Variation 1-4

A variation 1-4 of the first embodiment of the disclosure is described. Control information is obtained after it is checked that a capsule endoscope 10 is in a stable standing-still state at step S12 in the above-described variation 1-2; it is also possible to determine whether this is in the stable standing-still state on the basis of a calibration condition obtained in the above-described variation 1-3. In detail, it is determined that the capsule endoscope 10 is in the stable standing-still state when an actual distance between the capsule endoscope 10 and an external permanent magnet 31 is within a predetermined range (within an error range of ±small percent, for example) with respect to the distance between the capsule endoscope 10 and the external permanent magnet 31 obtained as the calibration condition.

According to the variation 1-4, it is possible to prevent a control state when the capsule endoscope 10 is pressed against an inner wall ST from being obtained as the control information at step S12.

Variation 1-5

Figure 10:
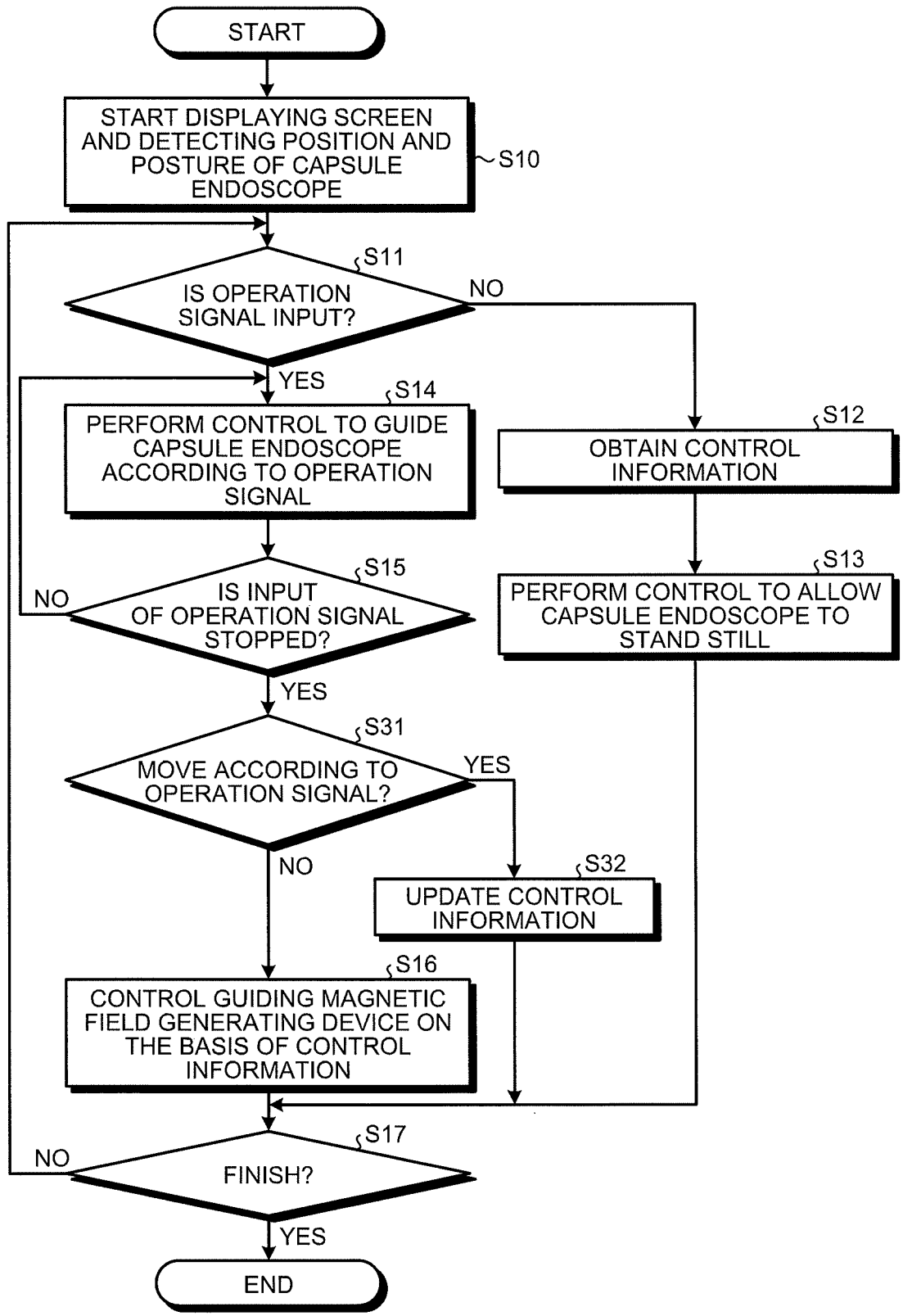
FIG. 10 is a flowchart illustrating operation of a control device in a variation 1-5 of the first embodiment of the disclosure.

A variation 1-5 of the first embodiment of the disclosure is described. FIG. 10 is a flowchart illustrating operation of a control device 40 in this variation. Among them, steps S10 to S15 are similar to those of the first embodiment.

When an input of an operation signal is stopped at step S15 (step S15: Yes), a control unit 47 determines whether a capsule endoscope 10 moves according to the operation signal on the basis of positional information of the capsule endoscope 10 output from an arithmetic unit 45 (step S31). That is to say, a displacement of the capsule endoscope 10 is obtained from a position of the capsule endoscope 10 when the operation signal is input at step S11 and a position of the capsule endoscope 10 when the input of the operation signal is stopped at step S15, and the displacement is compared with a motion amount of the capsule endoscope 10 corresponding to the operation signal. Alternatively, it is also possible to calculate an actual moving speed of the capsule endoscope 10 from the displacement of the capsule endoscope 10 and elapsed time and compare the moving speed with the moving speed of the capsule endoscope 10 corresponding to the operation signal.

The control unit 47 determines that the capsule endoscope 10 moves according to the operation signal when an error between the motion amount or the moving speed of the capsule endoscope 10 corresponding to the operation signal and actual displacement or moving speed of the capsule endoscope 10 is not larger than a threshold.

When the capsule endoscope 10 moves according to the operation signal (step S31: Yes), the control unit 47 updates control information to the control information indicating a current control state for a guiding magnetic field generating device 30 (step S32). Subsequent step S17 is similar to that of the first embodiment.

On the other hand, when the capsule endoscope 10 does not move according to the operation signal (step S31: No), the control unit 47 controls the guiding magnetic field generating device 30 on the basis of the already obtained control information (step S16). Step S17 thereafter is similar to that of the first embodiment.

According to the variation 1-5, when the capsule endoscope 10 moves according to operation on an operation input device 43, the control information used when controlling the guiding magnetic field generating device 30 after the input of the operation signal is stopped is updated, so that it is possible to control the guiding magnetic field generating device 30 on the basis of the newest control information set according to a position of the capsule endoscope 10 and an environment (a shape and the like of an organ).

Variation 1-6

Although magnetic attracting force acting on a capsule endoscope 10 when the capsule endoscope 10 is in a stable standing-still state or a distance between the capsule endoscope 10 which generates the magnetic attracting force and an external permanent magnet 31 is obtained as control information in the above-described first embodiment, a type of the control information is not limited to this.

For example, it is also possible to make a posture (elevation angle and turn angle) of the external permanent magnet 31 together with the distance between the capsule endoscope 10 and the external permanent magnet 31 the control information. In this case, when operation on an operation input device 43 is stopped, the stable standing-still state of the capsule endoscope 10 may be reproduced with higher accuracy.

Variation 1-7

An electric magnet may also be used in place of an external permanent magnet 31 in the above-described guiding magnetic field generating device 30. In this case, it is possible to change magnetic attracting force Fm acting on a capsule endoscope 10 by adjusting strength of a guiding magnetic field by controlling current or voltage to be supplied to the electric magnet. Also, it is possible to obtain magnitude of the current or voltage supplied to the electric magnet before starting operation or when starting operation on an operation input device 43 as control information at step S12 in FIG. 6.

Alternatively, it is also possible to obtain positional information of the capsule endoscope 10 as the control information in addition to the magnitude of the current or voltage.

In this case, it is possible to control the magnetic attracting force Fm acting on the capsule endoscope 10 with higher accuracy by adjusting a distance between the capsule endoscope 10 and the electric magnet together with the magnitude of the current or voltage.

Variation 1-8

Control in a case in which a specific gravity of a capsule endoscope 10 is made smaller than that of liquid W and the capsule endoscope 10 is guided by balance among buoyancy acting on the capsule endoscope 10, gravity, and vertically downward magnetic attracting force is described in the above-described first embodiment and variations 1-1 to 1-7. However, similar control may be also performed when the specific gravity of the capsule endoscope 10 is made larger than that of the liquid W. In this case, an external permanent magnet 31 (refer to FIG. 3) is arranged above a bed 21 on which a subject is placed and the capsule endoscope 10 is guided by the buoyancy acting on the capsule endoscope 10, the gravity, and vertically upward magnetic attracting force. Also, in this case, operation to move the capsule endoscope 10 vertically upward is input, and when the capsule endoscope 10 is brought into contact with an upper inner wall in the subject, control on a guiding magnetic field generating device 30 after the operation is finished is performed on the basis of control information before or when the operation is started.

Second Embodiment

Next, a second embodiment of the disclosure is described.

A configuration and operation of a capsule medical device guidance system according to the second embodiment are similar to those of the first embodiment as a whole (refer to FIGS. 1 and 6), and a control method in a case in which a capsule endoscope 10 is moved in a horizontal direction is described in the second embodiment. Meanwhile, although a case in which the capsule endoscope 10 is moved in an X direction is hereinafter described, similar control is performed also in a Y direction.

Figure 11A:
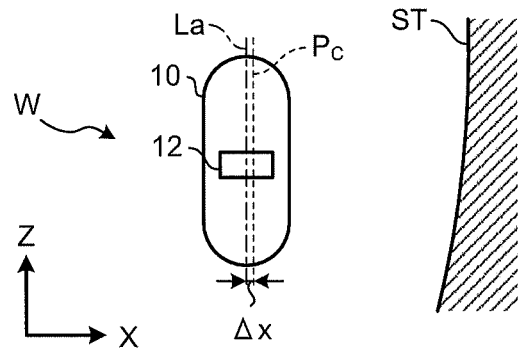
FIG. 11A is a schematic diagram for illustrating a method of guiding a capsule endoscope in a capsule medical device guidance system according to a second embodiment of the disclosure.

FIGS. 11A to 11D are schematic diagrams for illustrating a method of guiding the capsule endoscope 10 in the capsule medical device guidance system according to the second embodiment of the disclosure. Also, FIG. 12 is a graph for illustrating the control method according to presence of operation to move the capsule endoscope 10 in the horizontal direction. In the drawing, (a) of FIG. 12 illustrates the presence of the operation on the operation input device 43 (ON or OFF). Also, (b) of FIG. 12 illustrates a position in the horizontal direction (X direction) of the capsule endoscope 10 and a trapping axis $P_C$.

Operation of the capsule medical device guidance system according to the second embodiment is described with reference to FIG. 6. Meanwhile, steps S10 and S11 are similar to those of the first embodiment.

When an operation signal is not input from the operation input device 43 to a control unit 47 at step S11 (step S11: No, t=0 to $t_{21}$), the control unit 47 obtains control information indicating a current control state for a guiding magnetic field generating device 30 (step S12). In the second embodiment, as illustrated in FIG. 11A, a position $X_C$ of the capsule endoscope 10 (for example, long axis La) and a position $X_P$ of the trapping axis $P_C$ of the capsule endoscope 10 determined by a position of an external permanent magnet 31 (refer to FIG. 3) are obtained, and an error Δx being a relative relationship between the position $X_C$ of the capsule endoscope 10 and the position $X_P$ of the trapping axis $P_C$ is obtained as the control information.

At subsequent step S13, a guiding magnetic field controller 471 performs control to allow the capsule endoscope 10 to stand still on the guiding magnetic field generating device 30. Specifically, it is sufficient to allow the external permanent magnet 31 to stand still to prevent movement of the trapping axis $P_C$.

By repeating steps S12 and S13, the control information (error $\Delta x$) in a state in which a horizontal position of the capsule endoscope 10 is stable is obtained.

On the other hand, when the operation signal is input at step S11 (step S11: Yes, $t=t_{21}$ to $t_{23}$), the guiding magnetic field controller 471 performs control to guide the capsule endoscope 10 according to the operation signal input from the operation input device 43 (step S14).

Figure 11B:
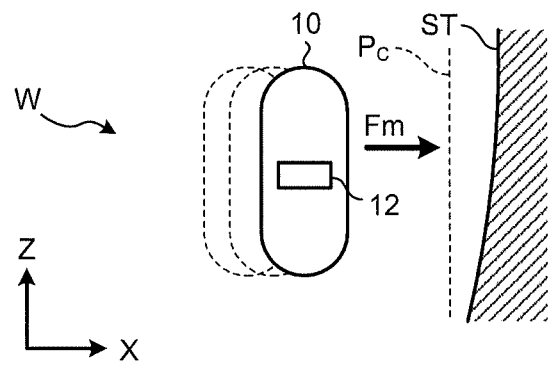
FIG. 11B is a schematic diagram for illustrating the method of guiding the capsule endoscope in the capsule medical device guidance system according to the second embodiment of the disclosure.
Figure 12:
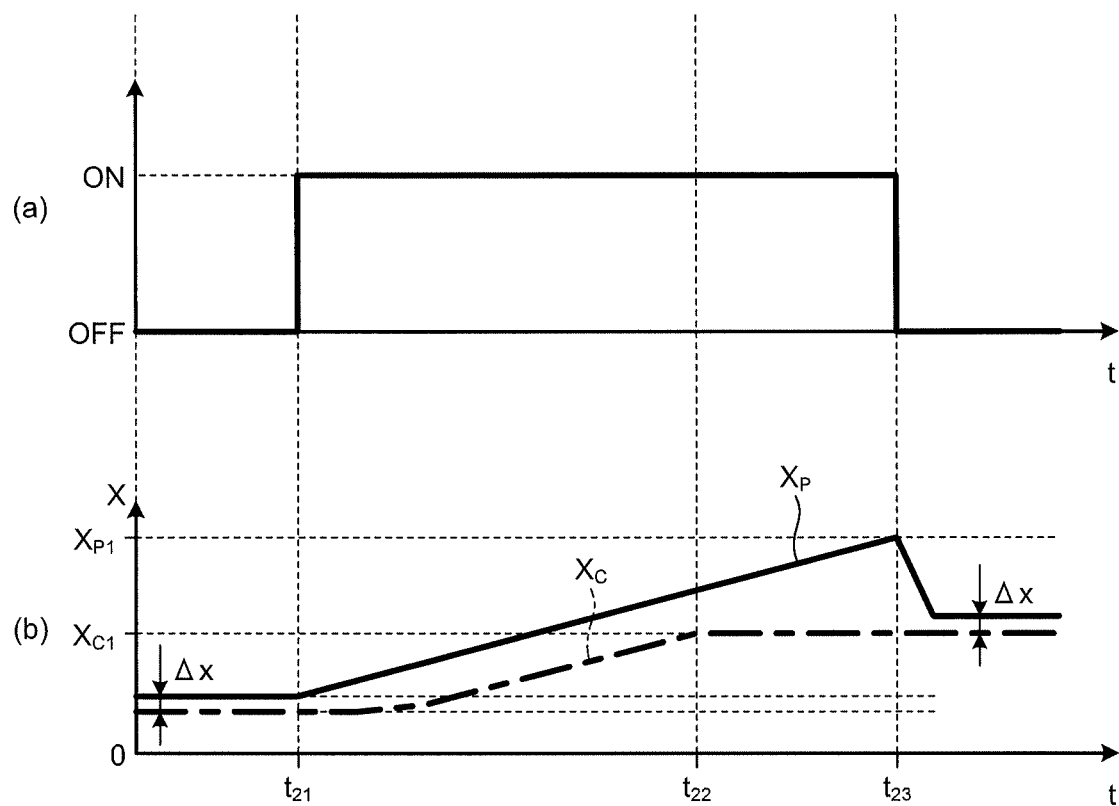
FIG. 12 is a graph for illustrating a control method according to presence of an operation input to move the capsule endoscope in a horizontal direction.

For example, when an operation input to guide the capsule endoscope 10 in the horizontal direction (X direction) is performed, the guiding magnetic field controller 471 moves the trapping axis $P_C$ in the X direction by allowing the guiding magnetic field generating device 30 to translate the external permanent magnet 31 in the X direction as illustrated in FIG. 11B. According to this, the capsule endoscope 10 moves following the trapping axis $P_C$ by magnetic attracting force Fm in a direction of the trapping axis $P_C$. Subsequent step S15 is similar to that of the first embodiment.

When the input of the operation signal is stopped at step S15 (step S15: Yes, $t=t_{23}$), the guiding magnetic field controller 471 controls the guiding magnetic field generating device 30 on the basis of the control information obtained at step S12 (step S16).

Figure 11C:
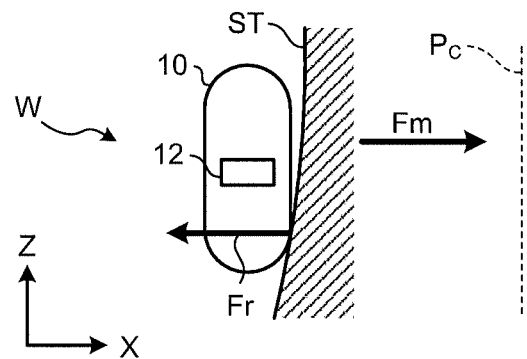
FIG. 11C is a schematic diagram for illustrating the method of guiding the capsule endoscope in the capsule medical device guidance system according to the second embodiment of the disclosure.

Herein, a case in which the capsule endoscope 10 is brought into contact with an inner wall ST on a side of an organ as illustrated in FIG. 11C is considered. In this case, as illustrated in $t=t_{22}$ to $t_{23}$ in FIG. 12, the position of the capsule endoscope 10 remains unchanged from $X_C=X_{C1}$. However, a user continuously performs operation on the operation input device 43 until the user recognizes that the capsule endoscope 10 is brought into contact with the inner wall ST from positional information and an image in a subject displayed on a display unit 42, for example. As a result, the trapping axis $P_C$ continuously moves over the inner wall ST.

At that time, the capsule endoscope 10 stands still by balance of the magnetic attracting force Fm in the direction of the trapping axis $P_C$ and vertical drag Fr received from the inner wall ST. That is to say, there is a gap between a state of the capsule endoscope 10 intended by the control for the guiding magnetic field generating device 30 (state in which this stands still in a position of the trapping axis $P_C$ if there is not the inner wall ST) and an actual state of the capsule endoscope 10 (state in which this stands still in the position of the inner wall ST).

Thereafter, when the control state for the guiding magnetic field generating device 30 is left unchanged when the user stops the operation on the operation input device 43 ($t=t_{23}$), a gap between the position $X_P=X_{P1}$ of the trapping axis $P_C$ and the position $X_C=X_{C1}$ of the capsule endoscope 10 is maintained as it is. In this case, when the operation to move the capsule endoscope 10 in the horizontal direction is performed on the operation input device 43 next time, the control of a guiding magnetic field according to the operation on the operation input device 43 must be started after the trapping axis $P_C$ is returned to the actual capsule endoscope 10. Therefore, responsiveness of the capsule endoscope 10 to the operation on the operation input device 43 is deteriorated.

Figure 11D:
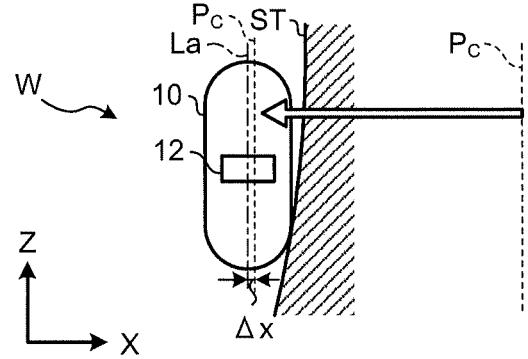
FIG. 11D is a schematic diagram for illustrating the method of guiding the capsule endoscope in the capsule medical device guidance system according to the second embodiment of the disclosure.

Therefore, when the operation on the operation input device 43 is stopped ($t=t_{23}$), the guiding magnetic field controller 471 obtains the position $X_C$ of the capsule endoscope 10 on the basis of the positional information output from an arithmetic unit 45 and controls the guiding magnetic field generating device 30 on the basis of the error $\Delta x$ obtained as the control information at step S12. Specifically, as illustrated in FIG. 11D, the guiding magnetic field generating device 30 is allowed to move the external permanent magnet 31 such that the error between the position $X_C$ of the capsule endoscope 10 and the position $X_P$ of the trapping axis $P_C$ is $\Delta x$. According to this, an input of next operation is waited after a state in which the capsule endoscope 10 is trapped by the trapping axis $P_C$ is reproduced. Subsequent step S17 is similar to that of the first embodiment.

As described above, in the second embodiment of the disclosure, the error $\Delta x$ between the position $X_C$ of the capsule endoscope 10 and the position $X_P$ of the trapping axis $P_C$ is obtained as the control information before starting or when starting the operation on the operation input device 43 and the guiding magnetic field generating device 30 is controlled such that the error $\Delta x$ is reproduced when the operation on the operation input device 43 stops. According to this, it is possible to eliminate the gap of the control generated during the operation. Therefore, when the operation on the operation input device 43 is performed next time, the control may be started from the state in which the capsule endoscope 10 is trapped in the position of the trapping axis $P_C$, so that the responsiveness of the capsule endoscope 10 to the operation may be improved.

Variation 2-1

In the above-described second embodiment also, as in the variation 1-1 of the first embodiment, control based on control information indicating a control state before starting or when starting operation may be executed only when a gap between the control state before starting or when starting the operation on an operation input device 43 and the control state when finishing the operation is large.

Specifically, when an input of an operation signal is stopped at step S15, a control unit 47 obtains a position $X_P$ of a trapping axis $P_C$ and a position $X_C$ of a capsule endoscope 10 at that time and calculates a distance therebetween as the control information when finishing the operation. When difference between the calculated distance and an error $\Delta x$ obtained as the control information at step S12 is larger than a threshold set in advance, control to move the trapping axis $P_C$ is performed such that the distance between the trapping axis $P_C$ and the capsule endoscope 10 becomes the error $\Delta x$.

Variation 2-2

Figure 13A:
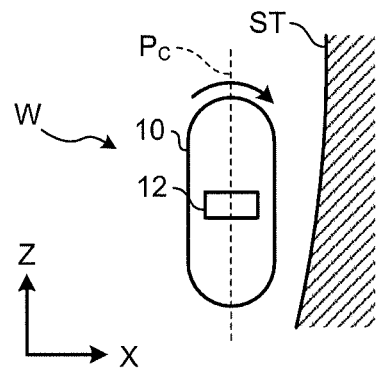
FIG. 13A is a schematic diagram for illustrating a control method according to a variation 2-2 of the second embodiment of the disclosure.
Figure 13B:
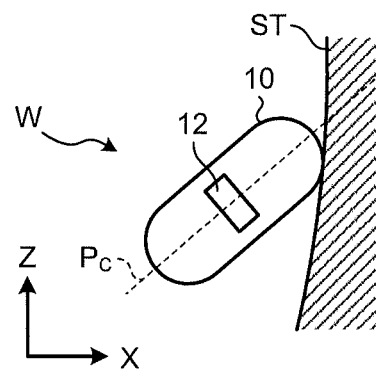
FIG. 13B is a schematic diagram for illustrating the control method according to the variation 2-2 of the second embodiment of the disclosure.
Figure 13C:
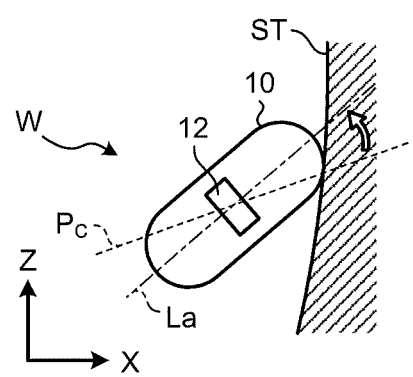
FIG. 13C is a schematic diagram for illustrating the control method according to the variation 2-2 of the second embodiment of the disclosure.

FIGS. 13A to 13C are schematic diagrams for illustrating a control method according to a variation 2-2 of the second embodiment of the disclosure. Although control in a case in which a capsule endoscope 10 is moved in an X direction is described in the above-described second embodiment, similar control may also be performed when a posture of the capsule endoscope 10 is changed, that is to say, when the capsule endoscope 10 is inclined or turned.

For example, a case in which a state of the capsule endoscope 10 is changed from an upright state to an inclined state as illustrated in FIG. 13A is considered. In this case, a trapping axis $P_C$ is inclined by rotation of an external permanent magnet 31 illustrated in FIG. 3 about the axis $Y_C$. According to this, the capsule endoscope 10 is inclined together with the trapping axis $P_C$ as illustrated in FIG. 13B.

Herein, when operation on an operation input device 43 is continued even though one end of the capsule endoscope 10 is brought into contact with an inner wall ST of an organ, only the trapping axis $P_C$ is further inclined with an inclination angle of the capsule endoscope 10 (long axis La) unchanged. That is to say, there is a gap between the state of the capsule endoscope 10 intended by control on a guiding magnetic field generating device 30 and an actual state of the capsule endoscope 10.

Therefore, before starting or when starting the operation on the operation input device 43, the control unit 47 obtains the inclination angle of the long axis La of the capsule endoscope 10 based on positional information output from an arithmetic unit 45 and an inclination angle of the trapping axis $P_C$ based on an angle about the axis $Y_C$ of the external permanent magnet 31 and obtains an error between the inclination angles as control information (refer to step S12 in FIG. 6). Then, the operation on the operation input device 43 is started (step S11: Yes), and when the operation is stopped thereafter (step S15: Yes), a guiding magnetic field controller 471 controls the guiding magnetic field generating device 30 such that there is the error obtained as the control information between the long axis La of the capsule endoscope 10 and the trapping axis $P_C$ as illustrated in FIG. 13C. According to this, it is possible to improve responsiveness of the capsule endoscope 10 when the operation is performed on the operation input device 43 next time.

Also, when the capsule endoscope 10 is turned, similar control may be performed on the basis of an angle between two axes where the long axis La of the capsule endoscope 10 and the trapping axis $P_C$ are projected on an XY plane.

Variation 2-3

In the above-described second embodiment also, it is possible to obtain control information after checking that a capsule endoscope 10 is in a stable standing-still state as in the variation 1-2 of the first embodiment. In the above-described second embodiment also, as in the variation 1-5 of the first embodiment, the control information may be updated only when the capsule endoscope 10 moves according to operation on an operation input device 43.

Variation 2-4

In the above-described second embodiment also, as in the variation 1-7 of the first embodiment, it is possible to use an electric magnet in place of an external permanent magnet 31. In this case, it is possible to translate, incline, or turn a trapping axis $P_C$ by translating, inclining, or rotating one electric magnet.

Alternatively, it is also possible to arrange a plurality of electric magnets in place of the external permanent magnet 31 to trap a capsule endoscope 10 in a synthetic magnetic field of magnetic fields generated by the electric magnets. In this case, it is possible to translate, incline, or turn the trapping axis $P_C$ by controlling the magnetic fields generated by a plurality of electric magnets to change the synthetic magnetic field.

Third Embodiment

Next, a third embodiment of the disclosure is described.

A configuration and operation of a capsule medical device guidance system according to the third embodiment are similar to those of the first embodiment as a whole (refer to FIGS. 1 and 6), and a control method in a case in which a capsule endoscope 10 is moved in a horizontal direction is described in the third embodiment. Meanwhile, although a case in which the capsule endoscope 10 is moved in an X direction is hereinafter described, similar control is performed also in a Y direction.

Figure 14A:
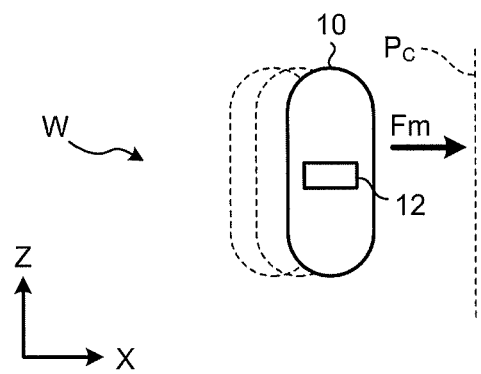
FIG. 14A is a schematic diagram for illustrating a method of guiding a capsule endoscope in a capsule medical device guidance system according to a third embodiment of the disclosure.
Figure 14B:
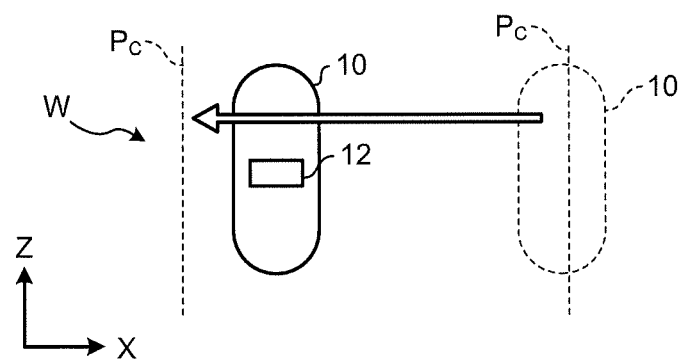
FIG. 14B is a schematic diagram for illustrating the method of guiding the capsule endoscope in the capsule medical device guidance system according to the third embodiment of the disclosure.
Figure 14C:
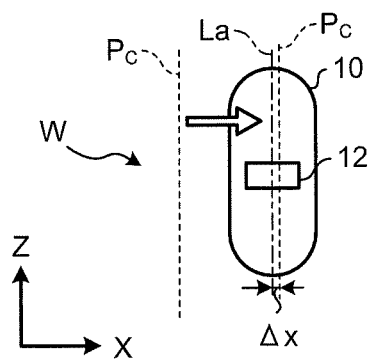
FIG. 14C is a schematic diagram for illustrating the method of guiding the capsule endoscope in the capsule medical device guidance system according to the third embodiment of the disclosure.
Figure 15:
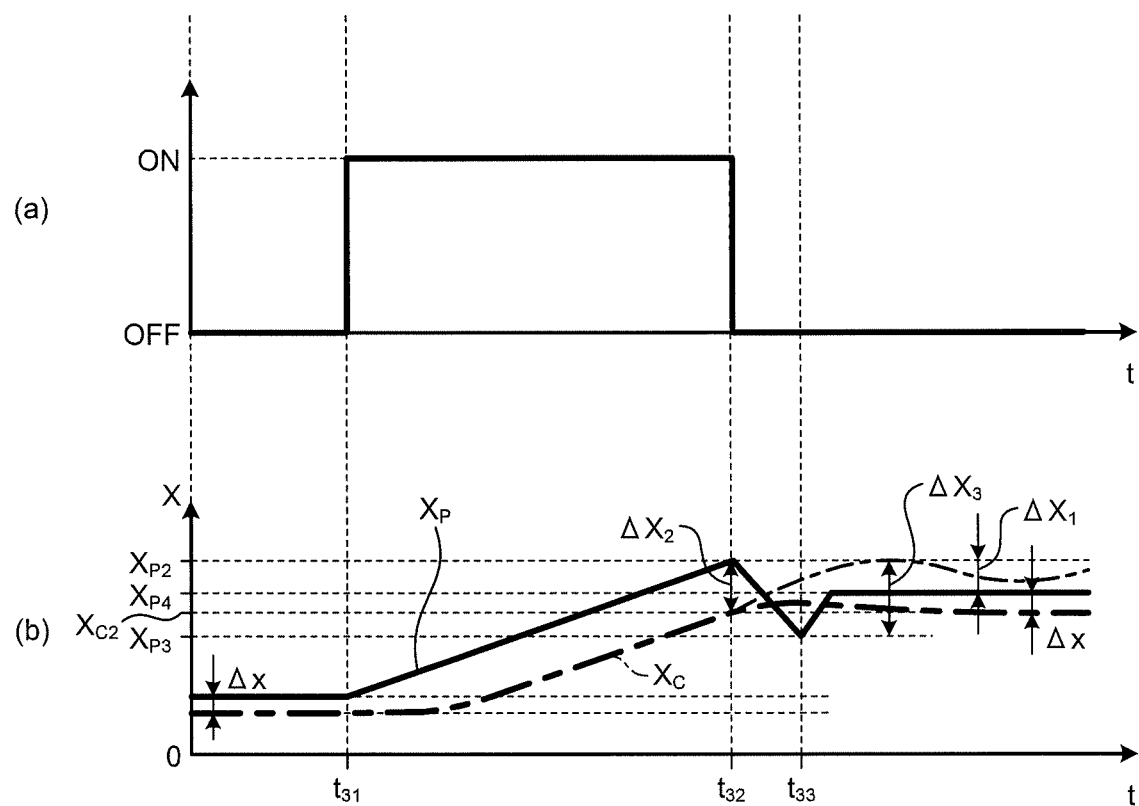
FIG. 15 is a graph for illustrating a control method according to presence of an operation input to move the capsule endoscope in a horizontal direction.

FIGS. 14A to 14C are schematic diagrams for illustrating a method of guiding the capsule endoscope 10 in the capsule medical device guidance system according to the third embodiment of the disclosure. Also, FIG. 15 is a graph for illustrating the control method according to presence of operation to move the capsule endoscope 10 in the horizontal direction. In the drawing, (a) of FIG. 15 illustrates the presence of operation on an operation input device 43 (ON or OFF). Also, (b) of FIG. 15 illustrates a position in the horizontal direction (X direction) of the capsule endoscope 10 and a trapping axis $P_C$.

Operation of the capsule medical device guidance system according to the third embodiment is described with reference to FIG. 6. Meanwhile, steps S10 and S11 are similar to those of the first embodiment.

When an operation signal is not input from the operation input device 43 to a control unit 47 at step S11 (step S11: No, t=0 to $t_{31}$), the control unit 47 obtains an error Δx between a position $X_C$ of the capsule endoscope 10 and a position $X_P$ of the trapping axis $P_C$ as control information as in the second embodiment (step S12). Step S13 thereafter is similar to that of the second embodiment.

On the other hand, when the operation signal is input at step S11 (step S11: Yes, t=$t_{31}$ to $t_{32}$), a guiding magnetic field controller 471 performs control to translate an external permanent magnet 31 in the X direction according to the operation signal to move the trapping axis $P_C$ (step S14) as in the second embodiment. According to this, the capsule endoscope 10 moves following the trapping axis $P_C$.

At that time, as illustrated in FIG. 14A, the capsule endoscope 10 moves while receiving magnetic attracting force Fm in a direction of the trapping axis $P_C$, so that this moves with slight delay from the trapping axis $P_C$. Therefore, there is a gap between the position $X_P$ of the trapping axis $P_C$ and the position $X_C$ of the capsule endoscope 10.

When the input of the operation signal is stopped at step S15 (step S15: Yes), the guiding magnetic field controller 471 controls the guiding magnetic field generating device 30 on the basis of the control information obtained at step S12 (step S16).

Herein, a case in which the capsule endoscope 10 is stopped in a position $X_{C2}$ desired by a user is considered. In this case, the user stops the operation on the operation input device 43 at the time (t=$t_{32}$) when recognizing that the capsule endoscope 10 arrives at the position $X_{C2}$ on the basis of positional information and the like displayed on a display unit 42. At that time, since the trapping axis $P_C$ precedes the capsule endoscope 10, if the trapping axis $P_C$ stops at a preceding position $X_{P2}$, the capsule endoscope 10 is attracted to the trapping axis $P_C$ to further move (refer to narrow dashed-dotted line in FIG. 15) As a result, it becomes impossible to stop the capsule endoscope 10 in the position $X_{C2}$ intended by the user.

Therefore, when the operation on the operation input device 43 is stopped (t=$t_{32}$), the guiding magnetic field controller 471 obtains the position $X_C$ of the capsule endoscope 10 on the basis of positional information output from an arithmetic unit 45 and controls the guiding magnetic field generating device 30 on the basis of the error Δx obtained as the control information at step S12. Specifically, the guiding magnetic field generating device 30 is allowed to move the external permanent magnet 31 such that the error between the position $X_C$ of the capsule endoscope 10 and the position $X_P$ of the trapping axis $P_C$ becomes Δx. At that time, as illustrated in FIGS. 14B and 14C, the trapping axis $P_C$ is briefly swung to a position $X_{P3}$ (t=$t_{33}$) beyond the capsule endoscope 10 and thereafter returned to a position $X_{P4}$ with the error $\Delta x$. That is to say, the trapping axis $P_C$ reciprocates over the capsule endoscope 10. According to this, it becomes possible to quickly stop the capsule endoscope 10 in the position $X_{C2}$ desired by the user.

A displacement $\Delta X_1$ from the position $X_{P2}$ of the trapping axis $P_C$ when the operation on the operation input device 43 stops to the final stopping position $X_{P4}$ becomes smaller than difference $\Delta X_2$ between the position $X_{P2}$ of the trapping axis $P_C$ and the position $X_{C2}$ of the capsule endoscope 10 by approximately an error $\Delta x$. Also, it is possible to determine a swing width of the trapping axis $P_C \Delta X_3 = X_{P2} - X_{P3}$ such that the displacement $\Delta X_1$ to the final stopping position $X_{P4}$ of the trapping axis $P_C$ is substantially half the same. Subsequent step S17 is similar to that of the first embodiment.

As described above, in the third embodiment of the disclosure, the error $\Delta x$ between the position $X_C$ of the capsule endoscope 10 and the position $X_P$ of the trapping axis $P_C$ is obtained as the control information before starting or when starting the operation on the operation input device 43 and the guiding magnetic field generating device 30 is controlled such that the error $\Delta x$ is reproduced when the operation on the operation input device 43 stops, so that it becomes possible to stop the capsule endoscope 10 in the position $X_{C2}$ intended by the user. At that time, the trapping axis $P_C$ is briefly swung to the position $X_{P3}$ beyond the position $X_{C2}$ of the capsule endoscope 10 and is returned to the final position $X_{P4}$, so that it becomes possible to quickly stop the capsule endoscope 10 in the position $X_{C2}$.

Variation 3-1

In the above-described third embodiment also, it is possible to obtain control information after checking that a capsule endoscope 10 is in a stable standing-still state as in the variation 1-2 of the first embodiment. In the above-described third embodiment also, as in the variation 1-5 of the first embodiment, the control information may be updated only when the capsule endoscope 10 moves according to operation on an operation input device 43.

Variation 3-2

In the above-described third embodiment also, as in the variation 1-7 of the first embodiment, it is possible to use an electric magnet in place of an external permanent magnet 31. When translating, inclining, or turning a trapping axis $P_C$, it is possible to translate, incline, or rotate one electric magnet or change a synthetic magnetic field by controlling magnetic fields generated by a plurality of electric magnets.

According to some embodiments, a magnetic field generator is controlled after operation is finished by using control information indicating a control state for the magnetic field generator before starting or when starting the operation on an operation input device, so that a relative relationship between a capsule medical device and a magnetic field generator before starting or when starting the operation may be reproduced. Therefore, even when a gap is generated between a control state for the capsule medical device and an actual state of the capsule medical device during an operation input, the gap may be quickly eliminated after the operation is finished and it becomes possible to improve responsiveness of the capsule medical device to the operation input.

Although a case in which a capsule endoscope 10 is moved in any of a vertical direction or a horizontal direction is described in the above-described first to third embodiments and variations thereof, it is also possible to simultaneously move the same in both the vertical direction and the horizontal direction. In this case, control similar to that of the first embodiment or the variations 1-1 to 1-7 may be performed for operation of a vertical direction component on the operation input device 43 and control similar to that of the second embodiment and the variations 2-1 to 2-4 or the third embodiment may be performed for operation of a horizontal direction component on the operation input device 43.

The above-described first to third embodiments and variations thereof are merely examples for carrying out the disclosure and the disclosure is not limited to them. Various inventions may be formed by appropriately combining a plurality of components disclosed in the first to third embodiments and the variations thereof of the disclosure. The present invention may be variously modified according to the specification and the like and it is obvious from the above-description that various other embodiments may be made within the scope of the present invention.

What is claimed is:

1. A capsule medical device guidance system comprising:
   a capsule medical device including a permanent magnet provided inside the capsule medical device, the capsule medical device being configured to be introduced into a subject;
   a magnetic field generator provided outside the subject and configured to generate a magnetic field to be applied to the capsule medical device; and
   a processor comprising hardware, wherein the processor is configured to:
      receive input operation information for changing at least one of a position and a posture of the capsule medical device;
      prior to receiving the input operation information, control the magnetic field generator to balance forces acting on the capsule medical device to bring the capsule medical device into a still state where the capsule medical device has substantially no movement relative to the subject;
      obtain control information for controlling the magnetic field generator to bring the capsule medical device into the still state;
      subsequent to obtaining the control information, when receiving the input operation information, control the magnetic field generator to change at least one of a position and a posture of the capsule medical device based on the input operation information; and
      subsequent to changing the at least one position and posture of the capsule medical device, when the input operation information stops, control the magnetic field generator by using the control information to maintain the capsule medical device in the still state at the at least one position and posture.

2. The capsule medical device guidance system according to claim 1, wherein
   the processor is further configured to:
      detect the position of the capsule medical device; and
      control the magnetic field generator, based on the detected position of the capsule medical device, such that the forces acting on the capsule medical device are balanced.

3. The capsule medical device guidance system according to claim 1, wherein the control information includes strength of magnetic attracting force acting on the permanent magnet by the magnetic field generated by the magnetic field generator.

4. The capsule medical device guidance system according to claim 1, wherein
   the processor is further configured to detect the position of the capsule medical device, and the control information includes a distance between the magnetic field generator and the capsule medical device, which is calculated based on the detected position of the capsule medical device.

5. The capsule medical device guidance system according to claim 1, wherein
the processor is further configured to detect the position of the capsule medical device, and
the control information includes a relative relationship between a position of a specific axis on which the capsule medical device is trapped in the magnetic field formed by the magnetic field generator and the detected position of the capsule medical device.

6. The capsule medical device guidance system according to claim 1, wherein
the processor is further configured to detect the posture of the capsule medical device, and
the control information includes a relative relationship between a direction of a specific axis on which the capsule medical device is trapped in the magnetic field formed by the magnetic field generator and the detected posture of the capsule medical device.

7. The capsule medical device guidance system according to claim 1, wherein the processor is configured to:
obtain control information for the magnetic field generator when the input operation information stops; and
control the magnetic field generator to change the at least one of the position and the posture of the capsule medical device only when a difference between the control information for the still state and the control information according when the input operation information is stopped is larger than a threshold.

8. The capsule medical device guidance system according to claim 1, wherein
the processor is further configured to:
detect the at least one of the position and the posture of the capsule medical device; and
obtain the control information when variation per unit time of the at least one of the position and the posture is not larger than a threshold.

9. The capsule medical device guidance system according to claim 1, wherein
the processor is further configured to:
detect the at least one of the position and the posture of the capsule medical device;
when the input operation information stops, determine whether the capsule medical device is guided according to the input operation information based on the at least one of the position and the posture; and
when the capsule medical device is guided according to the input operation information, update the control information to control information for the magnetic field generator when the input operation information stops.

10. The capsule medical device guidance system according to claim 1, wherein
the magnetic field generator is formed of an electric magnet with electric power supply to generate a magnetic field, and
the processor is configured to adjust electric power supplied to the electric magnet to change the magnetic field acting on the permanent magnet.

11. The capsule medical device guidance system according to claim 1, wherein
the magnetic field generator is formed of an electric magnet with electric power supply to generate a magnetic field, and the processor is configured to change at least one of a position and a posture of the electric magnet to change the magnetic field acting on the permanent magnet.

12. The capsule medical device guidance system according to claim 1, wherein
the magnetic field generator is formed of a plurality of electric magnets where each is supplied with electric power to generate a magnetic field, and
the processor is configured to adjust the electric power supplied to each of the electric magnets to change the magnetic field generated by each of the electric magnets.

13. The capsule medical device guidance system according to claim 3, wherein
the processor is configured to:
perform control to guide the capsule medical device being in a state in which the capsule medical device is in contact with an inner wall on an upper side or a lower side of the subject in a vertical direction of the subject to be separated from the inner wall in the vertical direction; and
obtain, as the control information before starting or when starting the input operation information, control information for the magnetic field generator when the capsule medical device shifts from the state in which the capsule medical device is in contact with the inner wall to a state in which the capsule medical device is not in contact with the inner wall.

14. The capsule medical device guidance system according to claim 3, wherein
the processor is configured to:
perform control to guide the capsule medical device being in a state in which the capsule medical device is in contact with an inner wall on an upper side or a lower side of the subject in a vertical direction of the subject to be separated from the inner wall in the vertical direction;
obtain second control information for the magnetic field generator when the capsule medical device shifts from the state in which the capsule medical device is in contact with the inner wall to a state in which the capsule medical device is not in contact with the inner wall; and
obtain, among pieces of control information for the magnetic field generator, at least one of the pieces of control information when a difference from the second control information is within a predetermined range as the control information before starting or when starting the input operation information.

15. A capsule medical device guidance system comprising a processor comprising hardware, wherein the processor is configured to:
receive input operation information for changing at least one of a position and a posture of a capsule medical device having a permanent magnet;
prior to receiving the input operation information, control a magnetic field generator configured to generate a magnetic field to balance forces acting on the capsule medical device to bring the capsule medical device into a still state where the capsule medical device has substantially no movement relative to the subject;
obtain control information for controlling the magnetic field generator to bring the capsule medical device into the still state;
subsequent to obtaining the control information, when receiving the input operation information, control the magnetic field generator to change at least one of a position and a posture of the capsule medical device based on the input operation information; and subsequent to changing the at least one position and posture of the capsule medical device, when the input operation information stops, control the magnetic field generator by using the control information to maintain the capsule medical device in the still state at the at least one position and posture.

* * * * *